(12) United States Patent
Oshima et al.

(10) Patent No.: US 10,586,333 B2
(45) Date of Patent: Mar. 10, 2020

(54) IMAGE PROCESSING APPARATUS, IMAGE PROCESSING METHOD AND IMAGE PROCESSING SYSTEM

(71) Applicant: Sony Corporation, Tokyo (JP)

(72) Inventors: Shiori Oshima, Kanagawa (JP);
Kazuhiro Nakagawa, Saitama (JP);
Eriko Matsui, Tokyo (JP)

(73) Assignee: Sony Corporation, Tokyo (JP)

(*) Notice: Subject to any disclaimer, the term of this patent is extended or adjusted under 35 U.S.C. 154(b) by 135 days.

(21) Appl. No.: 15/554,018

(22) PCT Filed: Mar. 1, 2016

(86) PCT No.: PCT/JP2016/001091
§ 371 (c)(1),
(2) Date: Aug. 28, 2017

(87) PCT Pub. No.: WO2016/139925
PCT Pub. Date: Sep. 9, 2016

(65) Prior Publication Data
US 2018/0053301 A1    Feb. 22, 2018

(30) Foreign Application Priority Data

Mar. 4, 2015   (JP) .................. 2015-042079
Oct. 20, 2015  (JP) .................. 2015-206519

(51) Int. Cl.
*G06T 7/00*      (2017.01)
*G06T 7/223*     (2017.01)
(Continued)

(52) U.S. Cl.
CPC .......... *G06T 7/0016* (2013.01); *G06F 19/321* (2013.01); *G06K 9/00127* (2013.01);
(Continued)

(58) Field of Classification Search
CPC ..... A61B 5/150022; A61B 5/14; A61B 5/145; A61B 5/7264; A61B 5/7267; C40B 70/00;
(Continued)

(56) References Cited

U.S. PATENT DOCUMENTS 5,031,099 A   7/1991  Kettler
5,655,028 A   8/1997  Soll et al.
(Continued)

FOREIGN PATENT DOCUMENTS

JP    2006-350739 A    12/2006
JP    2014-179061 A     9/2014
(Continued)

OTHER PUBLICATIONS

International Search Report and Written Opinion dated Jun. 17, 2016 in connection with International Application No. PCT/JP2016/001091.
(Continued)

*Primary Examiner* — Aklilu K Woldemariam
(74) *Attorney, Agent, or Firm* — Wolf, Greenfield & Sacks, P.C.

(57) ABSTRACT

According to some aspects, an image processing apparatus is provided. The image processing apparatus includes circuitry configured to receive at least two images of a biological sample and determine motion information for a plurality of regions of the at least two images. The motion information corresponds to motion of the biological sample. The circuitry is further configured to generate a graphical representation of at least two characteristic amounts. The at least two characteristic amounts correspond to a region of the plurality of regions and one characteristic amount of the at least two characteristic amounts is indicative of the motion information.

23 Claims, 25 Drawing Sheets

(51) Int. Cl.
*G06T 7/246* (2017.01)
*G06F 19/00* (2018.01)
*G06K 9/00* (2006.01)
*G16H 30/20* (2018.01)
*G06K 9/46* (2006.01)

(52) U.S. Cl.
CPC ............... *G06T 7/223* (2017.01); *G06T 7/246* (2017.01); *G06K 9/0014* (2013.01); *G06K 9/4642* (2013.01); *G06T 2207/10056* (2013.01); *G06T 2207/20021* (2013.01); *G06T 2207/20076* (2013.01); *G06T 2207/30024* (2013.01); *G06T 2207/30064* (2013.01); *G16H 30/20* (2018.01)

(58) Field of Classification Search
CPC ............... G11C 13/0019; G01N 1/312; G01N 15/1475; G01N 15/1468; G01N 2021/6439; G01N 35/00732; G01N 2800/50; G01N 33/57407; G02B 21/244; G02B 21/365; G02B 21/367; G06K 9/00127; G06K 9/00134; G06K 9/00; G06K 9/3233; G06K 9/627; G06T 7/60; G06T 7/0012; G06T 7/223; G06T 7/246; G06T 7/0016; G06T 7/20; G06T 2207/10056; G06T 7/248; G06T 7/0014; G01R 33/54; G01R 33/5608; G01R 33/5601; Y10T 436/11; Y10T 436/112499; Y10T 436/2575; G16H 30/20; B01F 2215/0427; B01F 2215/045; B01F 2215/0454; B01L 3/5085; G06N 3/0454; C12Q 1/6886; G06F 19/00; G06F 19/321; G09G 3/002
USPC ................ 382/128, 129, 130, 131, 132, 133
See application file for complete search history.

(56) References Cited

U.S. PATENT DOCUMENTS

| | | | | |
|---|---|---|---|---|
| 6,329,139 | B1* | 12/2001 | Nova | B01J 19/0046 209/597 |
| 6,800,249 | B2* | 10/2004 | de la Torre-Bueno | G01N 1/31 382/128 |
| 6,948,843 | B2* | 9/2005 | Laugharn, Jr. | B01F 11/02 366/127 |
| 7,154,091 | B2* | 12/2006 | Zewail | H01J 37/065 250/311 |
| 2003/0231791 | A1* | 12/2003 | Torre-Bueno | G01N 21/6428 382/133 |
| 2004/0076999 | A1* | 4/2004 | Faeldt | G06T 7/0012 435/6.18 |
| 2005/0185832 | A1* | 8/2005 | Douglass | G01N 1/312 382/133 |
| 2006/0034545 | A1 | 2/2006 | Mattes et al. | |
| 2006/0178833 | A1* | 8/2006 | Bauer | G01N 15/1475 702/19 |
| 2009/0036764 | A1* | 2/2009 | Rivas | A61B 5/14532 600/365 |
| 2009/0086314 | A1* | 4/2009 | Namba | G01N 21/6458 359/383 |
| 2011/0044524 | A1* | 2/2011 | Wang | G01R 33/54 382/131 |
| 2011/0204258 | A1 | 8/2011 | Heller et al. | |
| 2012/0155725 | A1* | 6/2012 | Bathe | G06T 7/20 382/128 |
| 2013/0026669 | A1* | 1/2013 | Beckett | B01F 11/0283 264/9 |
| 2014/0329269 | A1* | 11/2014 | Adey | G01N 1/04 435/30 |
| 2015/0023580 | A1 | 1/2015 | Wehnes et al. | |
| 2016/0321495 | A1* | 11/2016 | Chukka | G06T 7/0012 |
| 2016/0344156 | A1* | 11/2016 | Rothberg | H01S 3/1118 |

FOREIGN PATENT DOCUMENTS

| | | |
|---|---|---|
| WO | WO 98/29732 A1 | 7/1998 |
| WO | WO 2013/114510 A1 | 8/2013 |

OTHER PUBLICATIONS

International Preliminary Report on Patentability dated Sep. 14, 2017 in connection with International Application No. PCT/JP2016/001091.

Japanese Office Action dated Oct. 23, 2019 in connection with Japanese Application No. 2015-206519, and English translation thereof.

Nishikawa et al., Extraction and motion analysis of lung surface from thoracic 4D-MRI. Japan (Corporate Juridical Person). Jan. 21, 2010; vol. 109(407), p. 265-268.

* cited by examiner

Plot numbers: 686   Plot percentage: 16.75%

IMAGE PROCESSING APPARATUS, IMAGE PROCESSING METHOD AND IMAGE PROCESSING SYSTEM

CROSS REFERENCE TO RELATED APPLICATIONS

This application is a national stage filing under 35 U.S.C. 371 of International Patent Application No. PCT/JP2016/001091, filed Mar. 1, 2016, which claims priority to Japanese Patent Application JP2015-206519, filed Oct. 20, 2015 and Japanese Patent Application JP2015-042079, filed Mar. 4, 2015.

TECHNICAL FIELD

The present technology relates to an information processing apparatus, a program, an information processing method and an observation system usable to an image analysis in a biochemistry field.

BACKGROUND ART

As an image processing technology advances, an image analysis is used for analyzing cells and body tissues. Specifically, a movement analysis is done on images where an object to be observed such as cells is captured over time, a feature amount relating to a movement including a moving speed and a moving area can be extracted and visualized (see Patent Document 1, for example).

In the above-described technology, cells and body tissues that can be captured via a microscope etc. are used as an object to be analyzed. For example, it is applicable to a variety of analyses such as a cancer cell chemotaxis, a neuron cell outgrowth and a cardiac muscle cell pulsation.

Patent Document 1: Japanese Patent 2014-179061

SUMMARY OF INVENTION PROBLEM TO BE SOLVED BY THE INVENTION

However, when the image generated by visualizing the feature amount relating to the movement is referred, it is difficult to perceive quantitatively the movement of the object to be observed.

In view of the above-described circumstances, an object of the present technology is to provide an information processing apparatus, a program, an information processing method and an observation system suitable for analyzing quantitatively a movement of an object to be observed.

According to an aspect of the present application, an image processing apparatus is provided. The imaging processing apparatus includes circuitry configured to receive at least two images of a biological sample and determine motion information for a plurality of regions of the at least two images. The motion information corresponds to motion of the biological sample. The circuitry is further configured to generate a graphical representation of at least two characteristic amounts. The at least two characteristic amounts correspond to a region of the plurality of regions and one characteristic amount of the at least two characteristic amounts is indicative of the motion information.

According to an aspect of the present application, an imaging processing method is provided. The method includes receiving at least two images of a biological sample and determining motion information for a plurality of regions of the at least two images. The motion information corresponds to motion of the biological sample. The method includes generating a graphical representation of at least two characteristic amounts. The at least two characteristic amounts correspond to a region of the plurality of regions and one characteristic amount of the at least two characteristic amounts is indicative of the motion information.

According to an aspect of the present application, an imaging processing system is provided. The imaging processing system includes at least one image sensor configured to acquire at least two images of a biological sample. The imaging processing system further includes circuitry configured to receive at least two images of a biological sample and determine motion information for a plurality of regions of the at least two images. The motion information corresponds to motion of the biological sample. The circuitry is further configured to generate a graphical representation of at least two characteristic amounts. The at least two characteristic amounts correspond to a region of the plurality of regions and one characteristic amount of the at least two characteristic amounts is indicative of the motion information.

As described above, according to the present technology, it is possible to provide an information processing apparatus, a program, an information processing method and an observation system suitable for analyzing quantitatively a movement of an object to be observed. The effects herein described are not limited, and any effect described in the present disclosure may be exerted.

MODES FOR CARRYING OUT THE INVENTION

An observation system according to the embodiment will be described.

(Configuration of Observation System)

Figure 1:
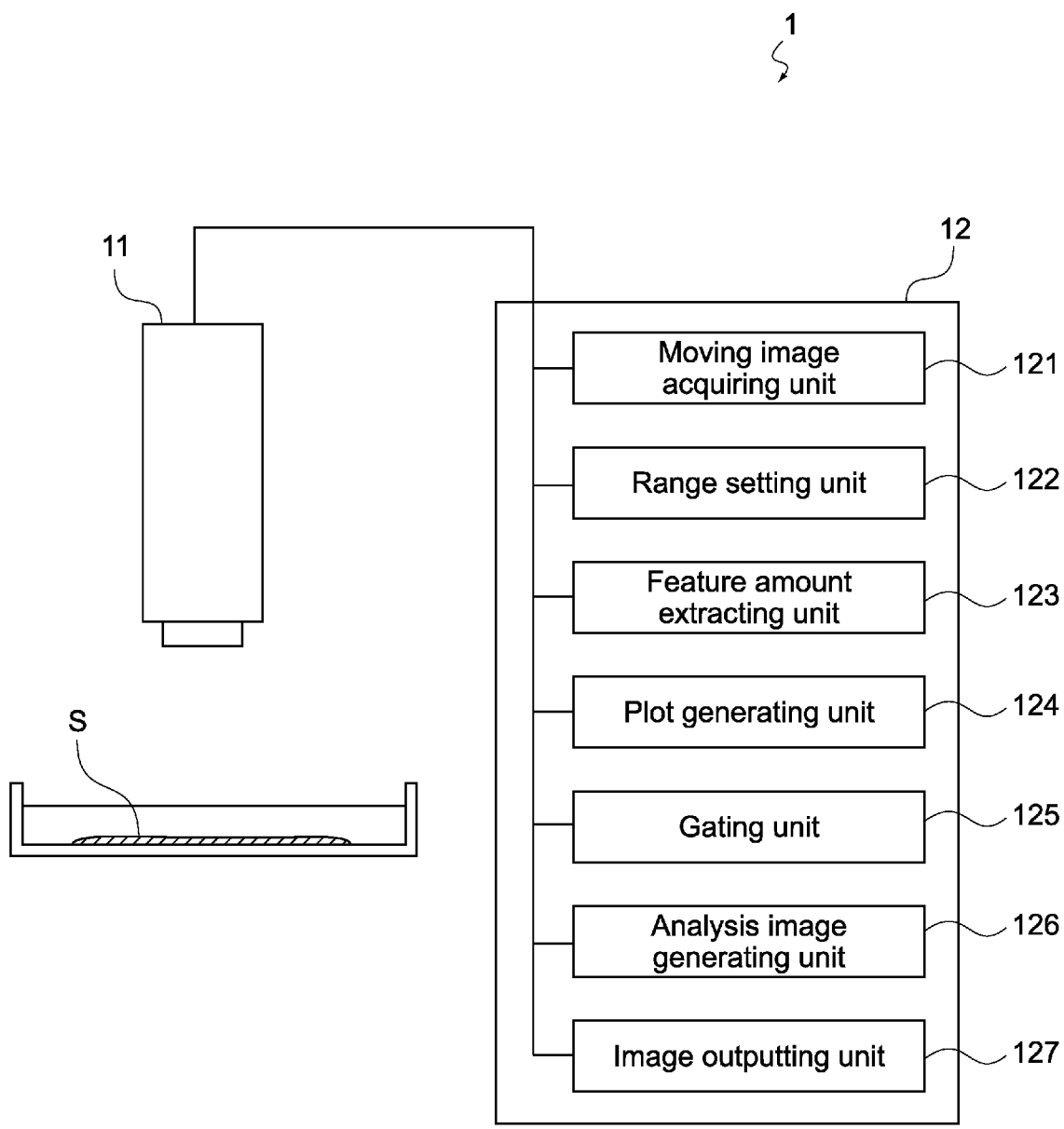
FIG. 1 A schematic diagram showing a configuration of an observation system according to an embodiment of the present technology.

FIG. 1 is a schematic diagram showing a configuration of an observation system 1 according to the embodiment. As shown in FIG. 1, the observation system 1 includes an image capturing apparatus 11 and an information processing apparatus. Also, FIG. 1 shows an object to be observed S. The object to be observed S may be cells cultured in a culture vessel, for example, may be body tissues, and may not especially be limited.

The image capturing apparatus 11 may capture the object to be observed S over time, and generate a moving image. The image capturing apparatus 11 may be a microscope including a microscope optical system and an image sensor, for example. Note that the image capturing apparatus 11 is not limited to the microscope, and may be any apparatus that can capture the object to be observed S over time.

The information processing apparatus 12 acquires and processes the moving image captured by the image capturing apparatus 11. The information processing apparatus 12 may be a personal computer, for example. Note that the information processing apparatus 12 may be integrally configured of the image capturing apparatus 11, or may be independent from the image capturing apparatus 11.

(Configuration of Information Processing Apparatus)

As shown in FIG. 1, the information processing apparatus 12 includes, as a functional configuration, a moving image acquiring unit 121, a range setting unit 122, a feature amount extracting unit 123, a plot generating unit 124, a gating unit 125, an analysis image generating unit 126 and an image outputting unit 127.

Figure 2:
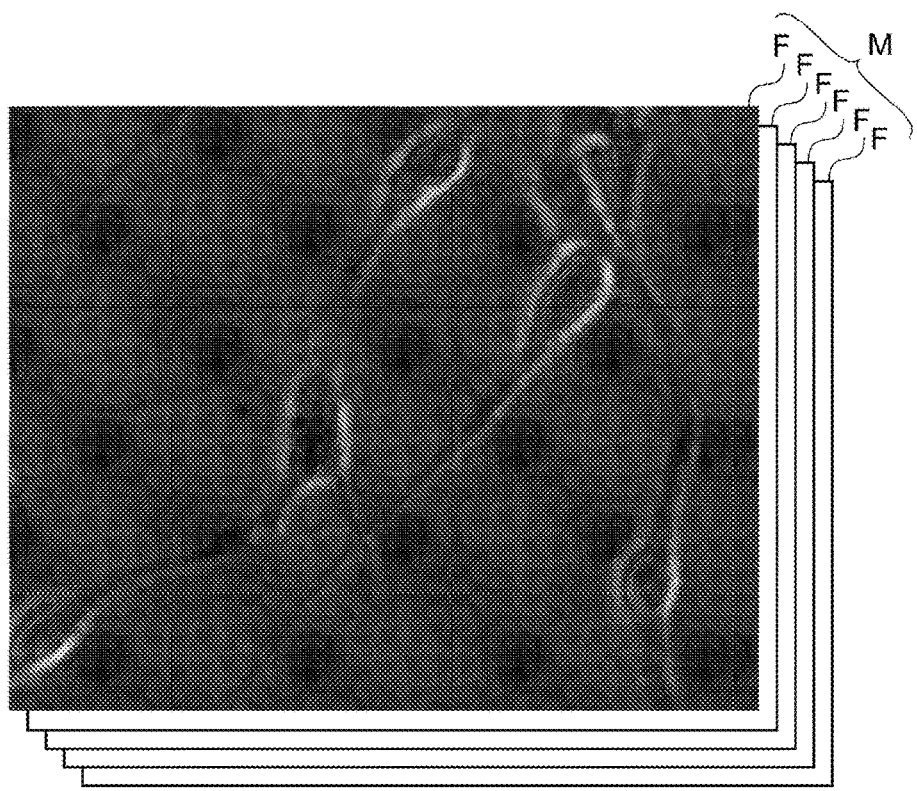
FIG. 2 A schematic diagram of a moving image acquired by a moving image acquiring unit of an information processing apparatus included in the observation system.

The moving image acquiring unit 121 acquires the moving image where the object to be observed S is captured over time. FIG. 2 is a schematic diagram showing a moving image acquired by the moving image acquiring unit 121. As shown in FIG. 2, the moving image M is configured of a plurality of images (frames) F captured continuously.

The number of the images F configuring the moving image M is optional, and may be several tens per second of the moving image M, for example. The moving image M is captured under the condition that a visual field to the object to be observed S is fixed, and may include a movement of the object to be observed S (a cell contractile movement, a substance transport, etc.).

The moving image acquiring unit 121 may acquire the moving image directly from the image capturing apparatus 11, or may acquire the moving image via a network or stored in a storage.

Figure 3:
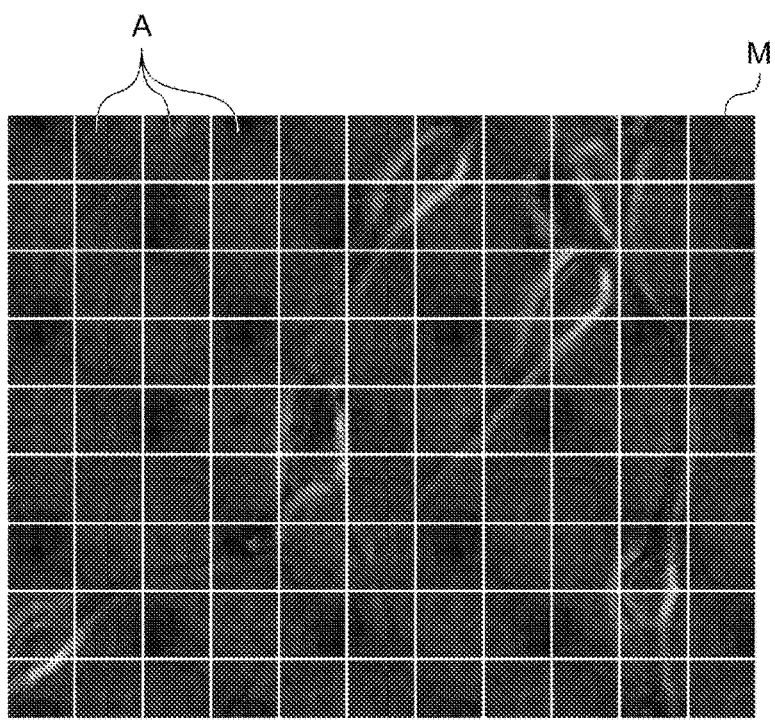
FIG. 3 A schematic diagram of an analysis range set by a range setting unit of the information processing apparatus.

The range setting unit 122 sets an analysis range in the moving image. FIG. 3 is a schematic diagram showing analysis ranges A set by the range setting unit 122. As shown in FIG. 3, the range setting unit 122 zones the moving image M into a plurality of areas having the same area to set the analysis ranges A. The size of each analysis range A is set in advance, or is determined by a user's designation. The size of each analysis range A may be several pixels to several tens pixel square.

Figure 4:
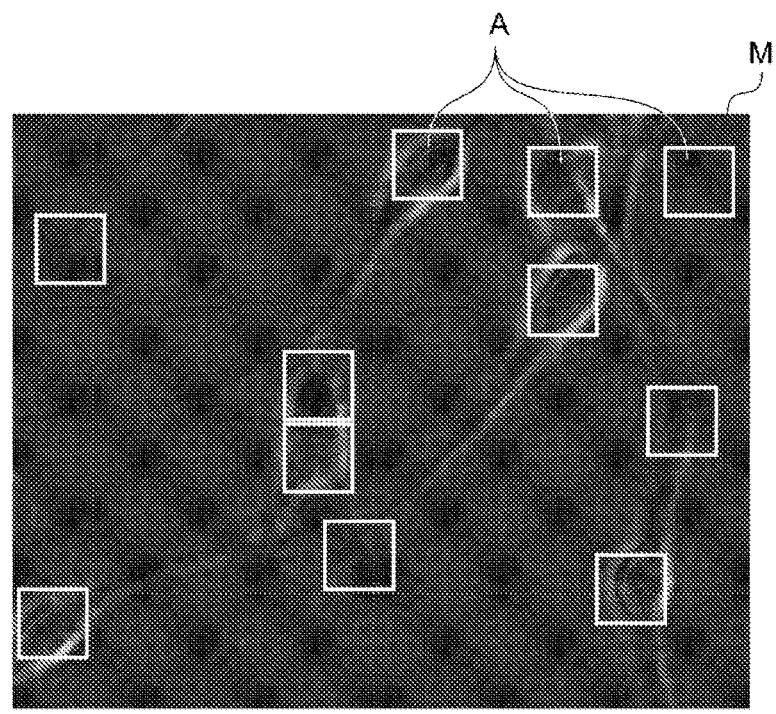
FIG. 4 A schematic diagram of an analysis range set by a range setting unit of the information processing apparatus.

The range setting unit 122 may set the analysis ranges A in a specific area of the moving image. FIG. 4 is a schematic diagram showing the analysis ranges A set in the specific area of the moving image M. The range setting unit 122 may set the analysis ranges A by a user's designation.

Also, the range setting unit 122 performs the image processing such as object detection processing on the moving image M, and may set the analysis ranges A based on the result. The range setting unit 122 may be set the analysis ranges A such that cell bodies detected in the moving image M are included, for example. The analysis ranges A set in the moving image M are also set to the same ranges in the respective images F.

The feature amount extracting unit 123 extracts the feature amount from each analysis range A. The feature amount extracting unit 123 may extract the feature amount that changes by a time (a time of capturing the moving image) (hereinafter, a first feature amount) and the feature amount that are not changed by a time (hereinafter, a second feature amount).

The first feature amount can be extracted from two or more of images F captured at different times. Specifically, the feature amount extracting unit 123 can compare at least two images included in the images F configuring the moving image M, and perform the movement analysis.

In the movement analysis, the two images are compared by a block matching method or the like to extract a movement of a corresponding pixel group between pixels as a movement vector. A magnitude of the movement vector represents a moving amount (i.e., a moving speed) between the images compared, and a direction of the movement vector represents a movement direction. By the movement analysis, the feature amount representing the movement property is calculated.

The feature amount extracting unit 123 calculates an average, maximum and minimum values, a standard deviation, a rate of acceleration, a frequency component, an integrated value, etc. of a space or a time in any segment to the feature amount representing the movement property for each analysis range A, thereby providing the first feature amount. Also, the feature amount extracting unit 123 calculates a percentage of the area having a movement (moving area) above a certain level in each analysis range A, thereby providing the first feature amount. Furthermore, the characteristic amount extracting unit 123 calculates a similarity degree to a specific waveform pattern for each analysis range A, or the number of occurrences of the specific waveform pattern, thereby providing the first characteristic amount.

The second feature amount can be extracted from one or more of images F. Specifically, the feature amount extracting unit 123 calculates a brightness value of each pixel in the images F, and calculates an average, maximum and minimum values, a standard deviation, a rate of acceleration, a frequency component, an integrated value, etc. of a space or a time in any segment to the brightness value for each analysis range A, thereby providing the second feature amount. Also, the feature amount extracting unit 123 calculates a percentage of the area (analysis area) where a substance exists in each analysis range A, thereby providing the second feature amount.

The feature amount extracting unit 123 can extract one or more of the first feature amounts and one or more of the second feature amounts for each analysis range. Also, the feature amount extracting unit 123 may extract two or more first feature amounts for each analysis range.

Figure 5:
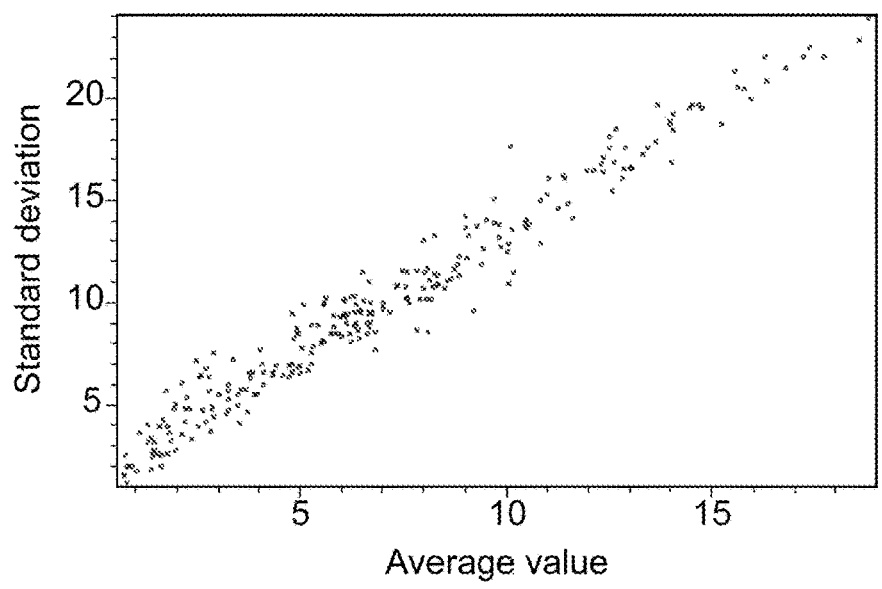
FIG. 5 A plot diagram generated by a plot generating unit of the information processing apparatus.

The plot generating unit 124 plots the feature amount calculated in each analysis range, and generates a plot diagram. FIG. 5 is an illustrative plot diagram generated by the plot generating unit 124. As shown in FIG. 5, the plot generating unit 124 plots the value in each analysis range with a movement average value (first feature amount) as an X axis and with a movement standard deviation (first feature amount) as an Y axis. Each plot in FIG. 5 is a plot for each analysis range.

In addition, the plot generating unit 124 can plot either of the first feature amount or the second feature amount, and any of the first feature amount and the second feature amount may be plotted on the X axis or the Y axis. The plot generating unit 124 may plot any two of the first feature amounts as the X axis and the Y axis.

Further, the plot by the plot generating unit 124 is not limited to a two-dimensional plot. The plot generating unit 124 can generate a multidimensional plot using three or more feature amounts including at least one first feature amount.

Figure 6:
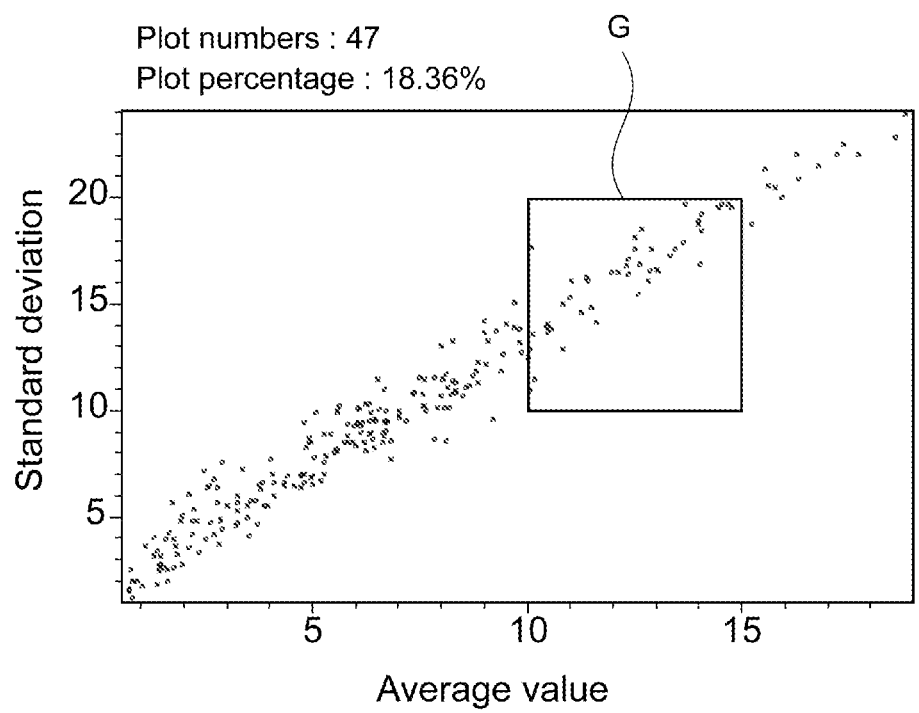
FIG. 6 A schematic diagram showing a gating mode in a gating unit of the information processing apparatus.

The gating unit 125 performs gating in the plot diagram generated by the plot generating unit 124. FIG. 6 is a schematic diagram showing a mode of the gating. As shown in FIG. 6, the gating unit 125 sets a gating range G in the plot diagram. The gating unit 125 can set the gating range G by a user's designation.

The gating range G can be specified by an upper limit and a lower limit of an X axis value and a Y axis value in the plot diagram shown in FIG. 6. Also, the gating range G may be specified by one or both of the upper limit and the lower limit of the X axis value, or one or both of the upper limit and the lower limit of the Y axis value. Furthermore, the gating range G may be the range having an optional shape in the plot diagram.

The gating unit 125 extracts (gates) only plots included in the gating range G, and does not extract the plots not included in the gating range G.

Also, the gating unit 125 can calculate the number of the plot(s) gated (included in the gating range G). FIG. 6 shows a calculation result (in FIG. 6, "plot numbers"). Also, the gating unit 125 can calculate a percentage of the plot(s) gated for all plots.

Figure 7:
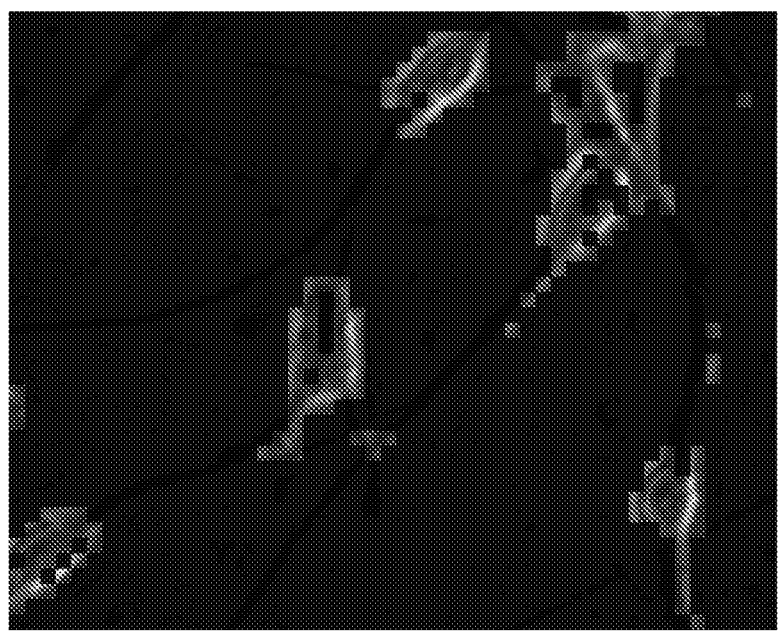
FIG. 7 An analysis image generated by an analysis image generating unit of the information processing apparatus.

The analysis image generating unit 126 visualizes a result of the gating, and generates the analysis image. FIG. 7 is an example of the analysis image. As shown in FIG. 7, the analysis image generating unit 126 applies a masking (black area) to the analysis range corresponding to the plot excluded by the gating (not including in the gating range G) to superimpose with the moving image, thereby generating the analysis image. Also, the analysis image generating unit 126 may visualize the result of the gating in other ways.

The image outputting unit 127 outputs images to a display apparatus, and displays them thereon. The image outputting unit 127 can display the plot diagram (see FIG. 6) generated by the plot generating unit 124. At this time, the image outputting unit 127 may display the number of the plot(s) calculated and gated by the gating unit 125 and its percentage together with the plot diagram (see FIG. 6). In addition, the image outputting unit 127 can display the analysis image (see FIG. 7) generated by the analysis image generating unit 126.

(Hardware Configuration of Information Processing Apparatus)

The above-described functional configuration of the information processing apparatus 12 can be realized by the hardware configuration shown below.

Figure 8:
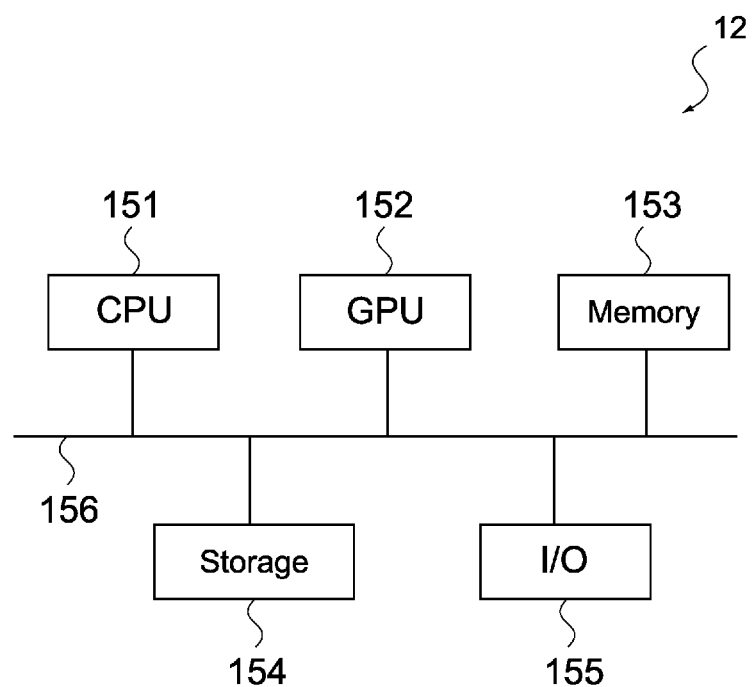
FIG. 8 A schematic diagram showing a hardware configuration of the information processing apparatus.

FIG. 8 is a schematic diagram showing a hardware configuration of the information processing apparatus 12. As shown in FIG. 8, the information processing apparatus 12 includes a CPU 151, a GPU 152, a memory 153, a storage 154 and an input and output unit (I/O) 155, as a hardware configuration. These are mutually connected by a bus 156.

A CPU (Central Processing Unit) 151 controls other components in accordance with a program stored in the memory 153, performs data processing in accordance with the program, and stores a processing result to the memory 153. The CPU 151 may be a microprocessor.

A GPU (Graphic Processing Unit) 152 is controlled by the CPU 151, and executes the image processing. The CPU 151 causes the GPU 152 to execute parallel arithmetic processing, and can extract the feature amount at a high speed. The GPU 152 may be a microprocessor.

The memory 153 stores a program and data executed by the CPU 151. The memory 153 may be a RAM (Random Access Memory).

The storage 154 stores a program and data. The storage 154 may be a HDD (hard disk drive) and an SSD (Solid State Drive).

The input/output unit 155 receives an input to the information processing apparatus 12, and supplies an output from the information processing apparatus 12 to outside. The input/output unit 155 includes an input device such as a keyboard and a mouse, an output device such as a display, and a connection interface such as a network.

The hardware configuration of the information processing apparatus 12 is not limited to one shown here, and may be the one that realizes the functional configuration of the information processing apparatus 12. Alternatively, a part or all of the hardware configuration may exist on the network.

(Operation of Information Processing Apparatus)

Figure 9:
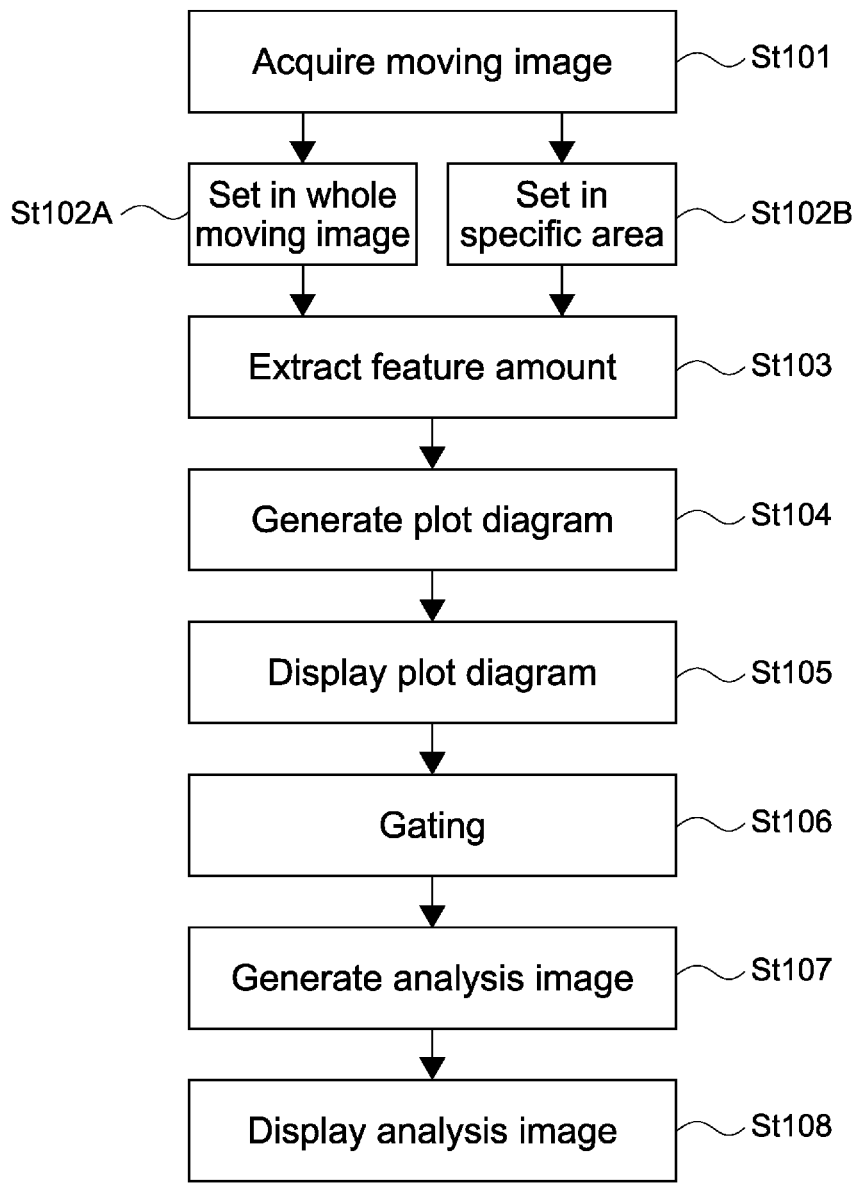
FIG. 9 A flow chart showing an operation of the information processing apparatus.

FIG. 9 is a flow chart showing an operation of the information processing apparatus 12.

As shown in FIG. 9, the moving image acquiring unit 121 acquires the moving image (St101). The moving image is provided by capturing the object to be observed over time, as described above. The moving image acquiring unit 121 supplies the moving image acquired to the range setting unit 122.

The range setting unit 122 sets the analysis range in the moving image. The range setting unit 122 may set the analysis range by zoning the whole moving image into a plurality of areas (St102A), or may set the analysis range only at the specific area (St102B). The range setting unit 122 supplies the moving image where the analysis range is set to the feature amount extracting unit 123.

The feature amount extracting unit 123 execute the analysis processing on the moving image, and extracts the feature amount for each analysis range (St103). The feature amount includes at least one of the first feature amount and the second feature amount, or includes at least two first feature amounts. The feature amount extracting unit 123 supplies the feature amount extracted to the plot generating unit 124.

The plot generating unit 124 plots the feature amount per analysis range, and generates the plot diagram (St104). The plot generating unit 124 may plot the first feature amount and the second feature amount as the X axis and the Y axis. Also, the plot generating unit 124 may plot the two first feature amounts as the X axis and the Y axis. The plot generating unit 124 supplies the plot diagram generated to the image outputting unit 127.

The image outputting unit 127 outputs the plot diagram to the display apparatus, and displays the plot diagram on the display apparatus (St105). A user can determine the gating range by referring to the plot diagram. The gating unit 125 may supply the number of the plots and the percentage included in the gating range designated to the image outputting unit 127, and may display them thereon.

The gating unit 125 performs the gating by utilizing the gating range designated (St106). The gating unit 125 supplies the analysis range corresponding to the gated plot (included in the gating range) to the analysis image generating unit 126.

The analysis image generating unit 126 visualizes the result of the gating, and generates the analysis image (St107). The analysis image generating unit 126 supplies the analysis image to the image outputting unit 127.

The image outputting unit 127 outputs the analysis image to the display apparatus, and displays the analysis image on the display apparatus (St108). When the gating range is changed, the gating unit 125 performs the gating using a new gating range, and the analysis image generating unit 126 can update and display the analysis image.

The information processing apparatus 12 performs the above-described operations. By using the information processing apparatus 12, the movement of the object to be observed (such as movement amount and moving area) can be quantitatively evaluated, and the evaluation result can be visually perceived.

Alternative Embodiment

The information processing apparatus 12 can analyze two or more moving images by comparing them. Hereinafter, the moving images analyzed by the information processing apparatus 12 are defined as the first moving image and the second moving image.

The first moving image and the second moving image are provided by capturing the object to be observed under different observation conditions. Specifically, the object to be observed is captured for a long time (for example, about several hours) to provide the first moving image, and the object to be observed is captured for a short time (for example, about several seconds) in the same visual field of first moving image to provide the second moving image. Alternatively, the first moving image provided by capturing the object to be observed for a long time may be extracted for a certain period of time to provide the second moving image.

Further, the first moving image and the second moving image may be provided by capturing the object to be observed under different culture environments. Specifically, the object to be observed is captured under a normal condition to provide the first moving image, and the object to be observed is captured by changing the culture environment in the same visual field of first moving image to provide the second moving image. The culture environment is changed by selecting administration of a medical agent or not, selecting a time from the administration of the medical agent, selecting a concentration of the medical agent, for example.

The information processing apparatus 12 can extract the feature amounts from the first moving image and the second moving image by the above-described method, and generate the plot diagram. Specifically, when the moving image acquiring unit 121 acquires the first moving image, the range setting unit 122 sets the analysis range in the first moving image. The feature amount extracting unit 123 extracts the feature amount from each analysis range.

Further, when the moving image acquiring unit 121 acquires the second moving image, the range setting unit 122 sets the analysis range in the second moving image. At this time, the range setting unit 122 sets the analysis range having the same arrangement as the first moving image. The feature amount extracting unit 123 extracts the feature amount same as the feature amount extracted in the first moving image from each analysis range.

Figure 10:
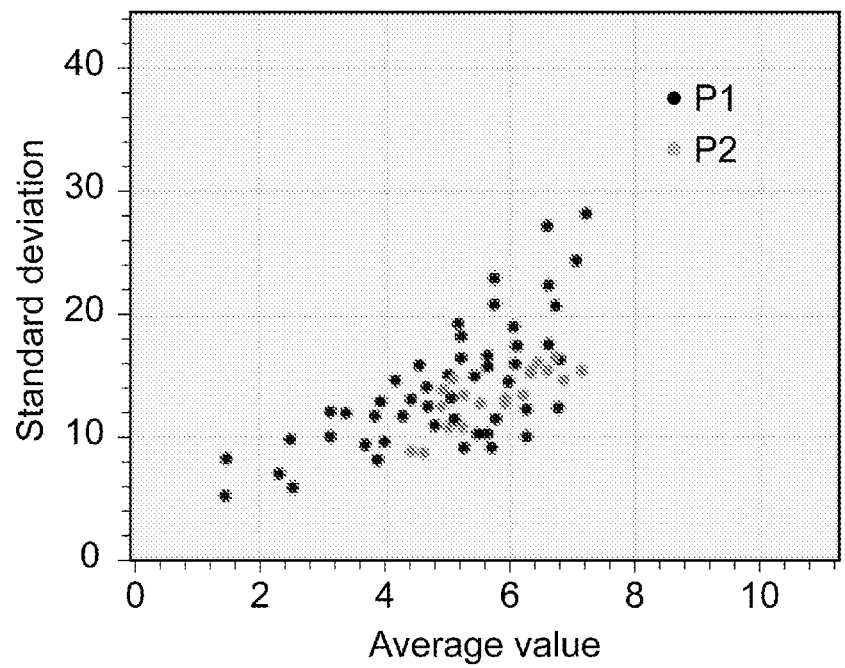
FIG. 10 A plot diagram generated by a plot generating unit of the information processing apparatus included in an observation system according to an alternative embodiment of the present technology.

The plot generating unit 124 plots the feature amount extracted from the first moving image and the feature amount extracted from the second moving image to generate one plot diagram. FIG. 10 shows the plot diagram. As shown in FIG. 10, the plot diagram includes a plot P1 of the feature amount extracted from the first moving image and a plot P2 of the feature amount extracted from the second moving image.

In this manner, as the plot P1 and the plot P2 are included one plot diagram, it is possible to provide a correlation between feature amounts of the first moving image and the second moving image.

For example, when the captured time of the first moving image is different from that of the second moving image, movement average values are compared, thereby providing a correlation between a movement of cells for several hours (cell migration etc.) and a movement of cells for several seconds (pseudopod movement, etc.).

Also, when the medical agent is administered or not on the first moving image and the second moving image, it is possible to evaluate an effect by the administration of the medical agent by comparing a maximum value of the movement.

After the plot diagram is generated, the gating unit 125 may perform the gating, and the analysis image generating unit 128 may generate the analysis image, as described above. The gating unit 125 may perform the gating on both of the plot P1 and the plot P2 in one gating range, or may perform the gating in different gating ranges for the plot P1 and the plot P2. The analysis image generating unit 128 may generate the analysis image for the first moving image and the analysis image for the second moving image separately.

Application Embodiments

Figure 11:
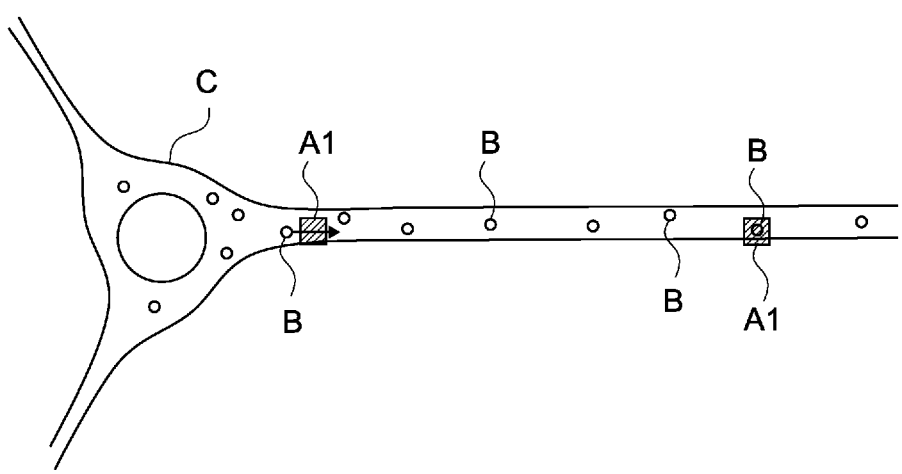
FIG. 11 A schematic diagram of an object to be observed in an application embodiment of the present technology.

The information processing apparatus 12 can be used for evaluation of an inter-cellular transport. FIG. 11 is a schematic diagram showing an intercellular transport, and shows that a cell C transports substances B.

When the moving image acquiring unit 121 acquires the moving image where the cell C is captured over time, the range setting unit 122 zones the moving image into a plurality of areas to set the analysis range. In the moving image, as shown in FIG. 11, the analysis ranges where the substances B are passed are denoted as analysis ranges A1, and the analysis ranges where a transport of the substances B is retarded are denoted as analysis ranges A2.

Figure 12:
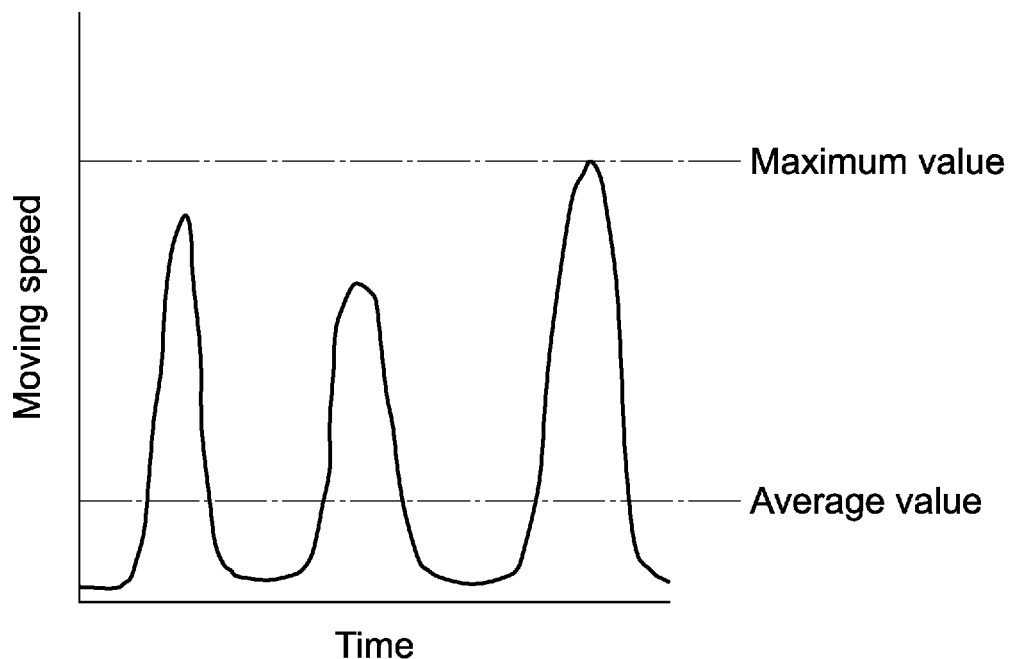
FIG. 12 A graph showing a time change extracted by a feature amount extracting unit of an information processing apparatus included in an observation system according to an application embodiment of the present technology.
Figure 13:
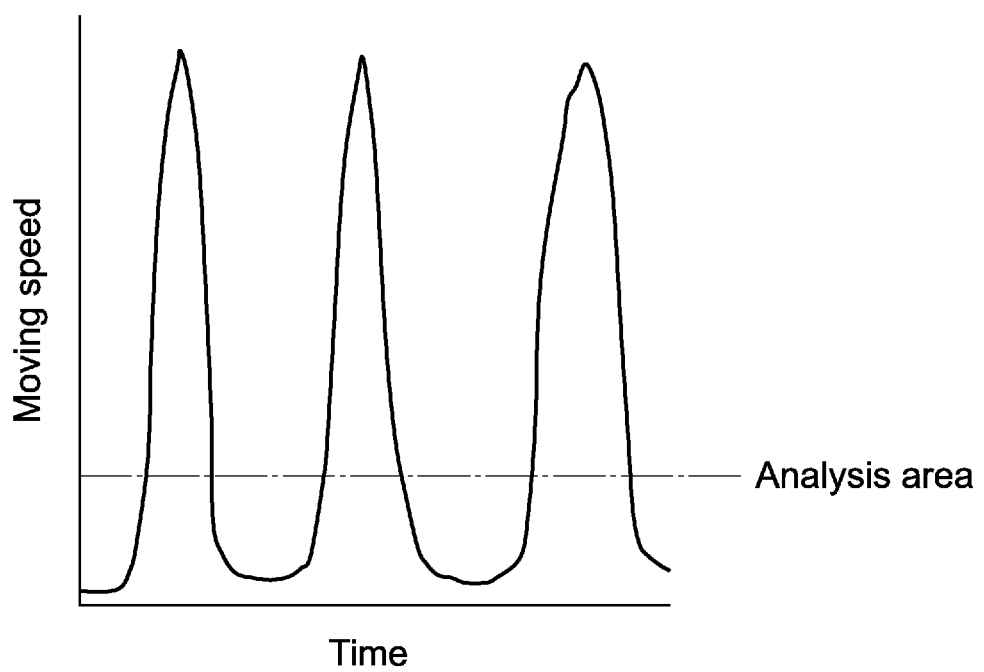
FIG. 13 A graph showing a time change of a feature amount extracted by the feature amount extracting unit of the information processing apparatus.

The feature amount extracting unit 123 extracts the feature amount for each analysis range. FIG. 12 shows a time change of the moving speed extracted in the analysis ranges A1. FIG. 13 shows a time change of the moving area extracted in the analysis ranges A1. In FIG. 12 and FIG. 13, there are peaks derived from the pass of the substances B.

Figure 14:
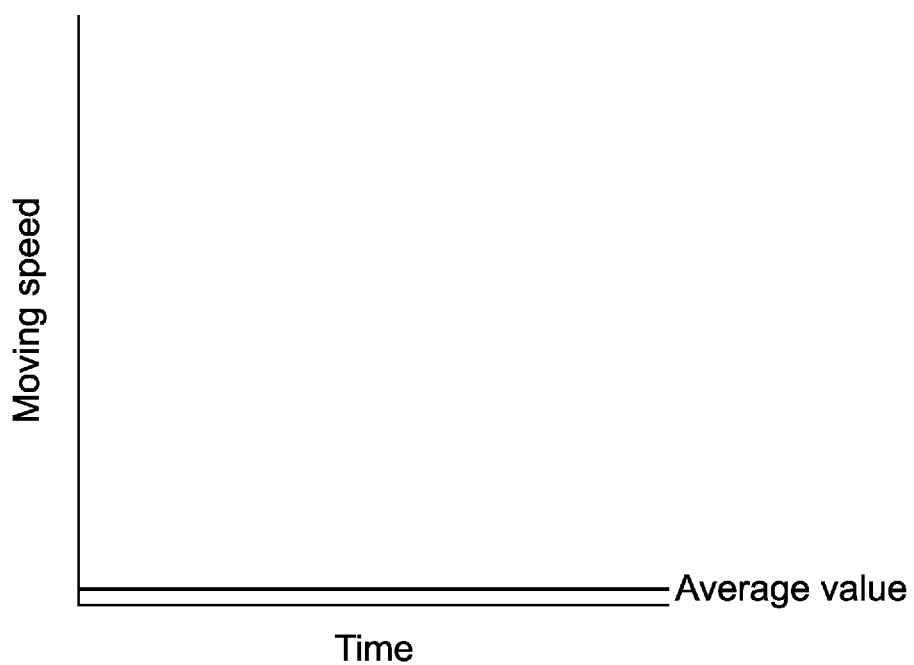
FIG. 14 A graph showing a time change of a feature amount extracted by the feature amount extracting unit of the information processing apparatus.
Figure 15:
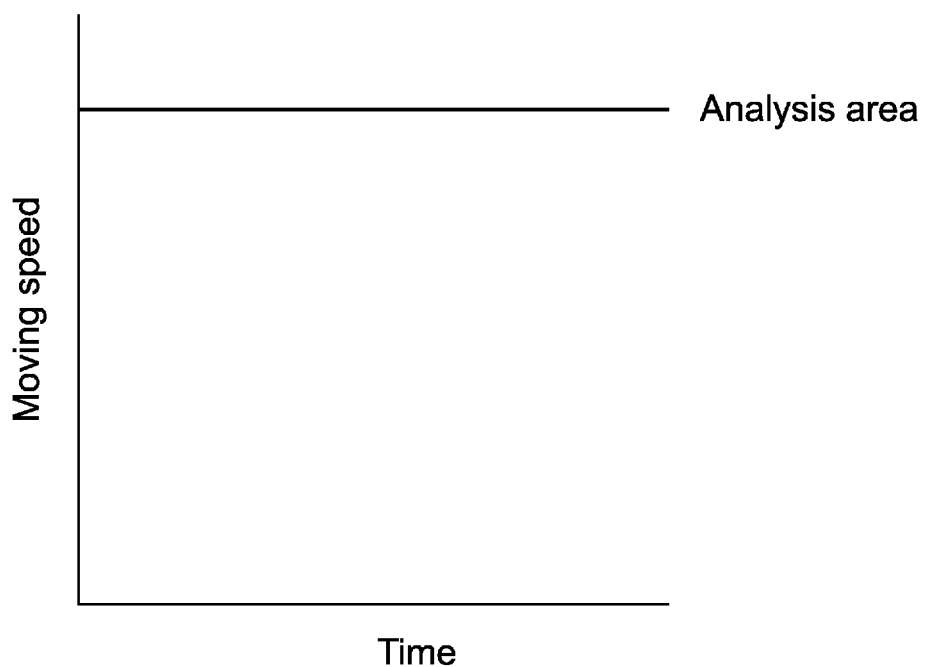
FIG. 15 A graph showing a time change of a feature amount extracted by the feature amount extracting unit of the information processing apparatus.

FIG. 14 shows a time change of the moving speed extracted in the analysis ranges A2. FIG. 15 shows a time change of the moving area extracted in the analysis ranges A2. In FIG. 14 and FIG. 15, there are no peaks derived from the pass of the substances B.

Figure 16:
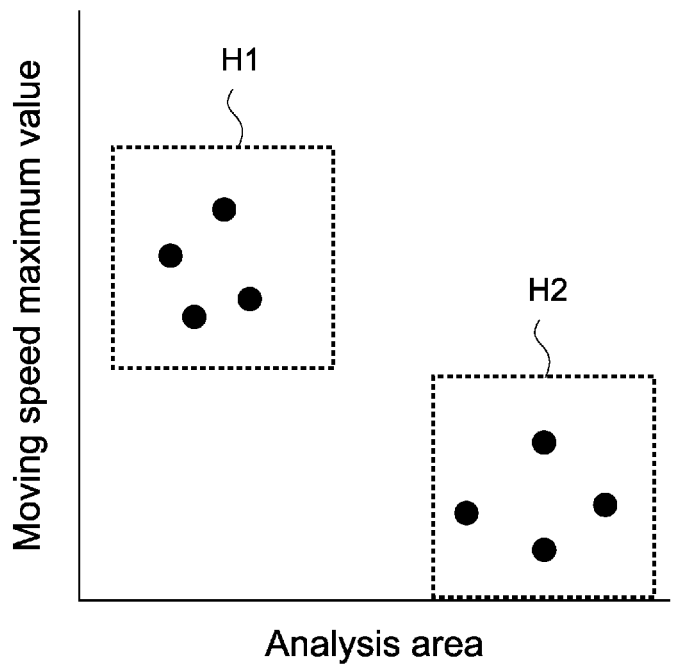
FIG. 16 A plot diagram generated by a plot generating unit of the information processing apparatus.

The plot generating unit 124 plots the feature amount extracted by the feature amount extracting unit 123, and generates the plot diagram. FIG. 16 is a plot diagram with the analysis area as the X axis and with a maximum value of the moving speed as the Y axis. As shown in FIG. 16, a coordinate (H1 in FIG. 16) and a coordinate (H2 in FIG. 16) are different. In the coordinate (H1 in FIG. 16), the plot of the analysis range (such as the analysis ranges A1) where the substance transfer is active is positioned. In the coordinate (H2 in FIG. 16), the plot of the analysis range (such as the analysis ranges A2) where the substance transfer is retarded is positioned.

Accordingly, by using the plot diagram shown in FIG. 16, it is possible to evaluate a frequency of the substance transfer, a speed, a retardation rate, or the like can be evaluated per analysis range of the moving image. For the evaluation of the substance transfer, the feature amounts such as the movement average value, the standard deviation and the moving area can be used other than the maximum value of the movement of the moving speed and the analysis area.

(Embodiments) Using the information processing apparatus described in the above-described embodiments, the moving image was analyzed to generate the plot diagram.

Figure 17:
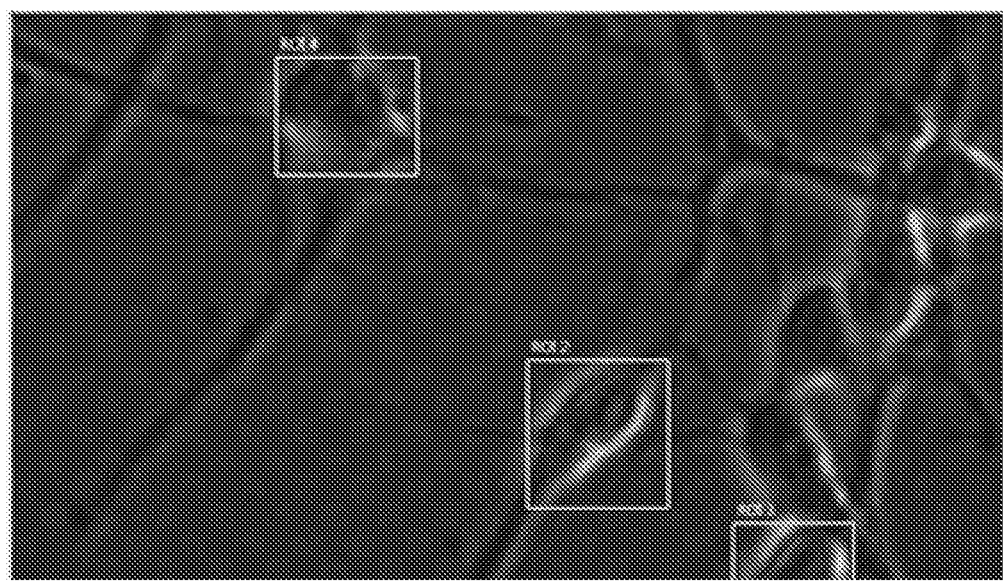
FIG. 17 A moving image according to an embodiment of the present technology.

FIG. 17 shows a moving image to be analyzed. The whole moving image shown in FIG. 17 was zoned to set the analysis range, and a variety of feature amounts were calculated for each analysis range. The feature amounts calculated are an average value of a moving speed, a maximum value, a standard deviation, a rate of acceleration, a moving area and an analysis area for each analysis range.

Figure 18:
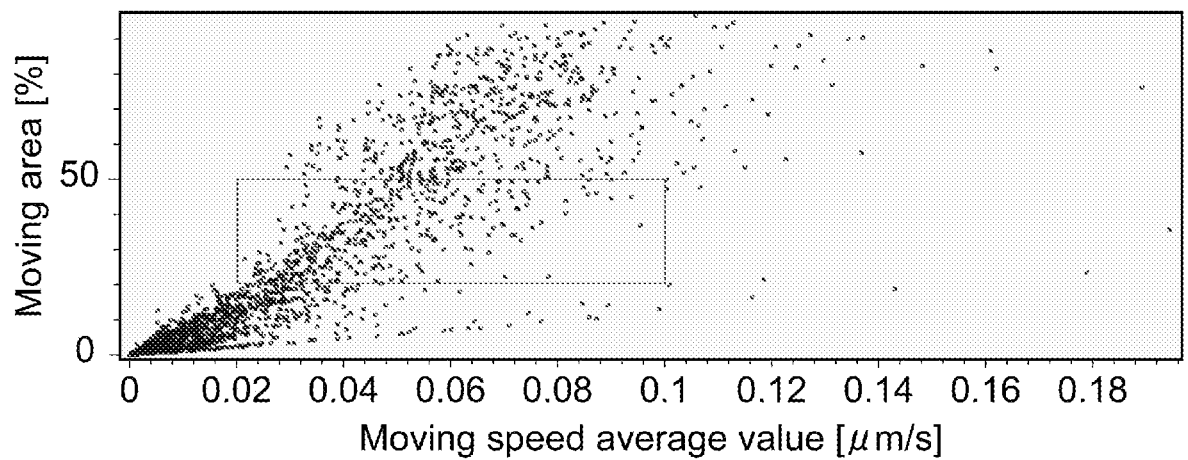
FIG. 18 A plot diagram according to an embodiment of the present technology.

FIG. 18 is a plot with the average value of the moving speed as the X axis, and with the moving area as the Y axis. As shown in FIG. 18, it shows that as the average value of the moving speed is increased, the moving area tends to be increased.

Using the information processing apparatus as described in the above embodiment, a movement of lung cancer cells was analyzed.

Figure 19:
FIG. 19 A moving image according to an embodiment of the present technology.
Figure 20:
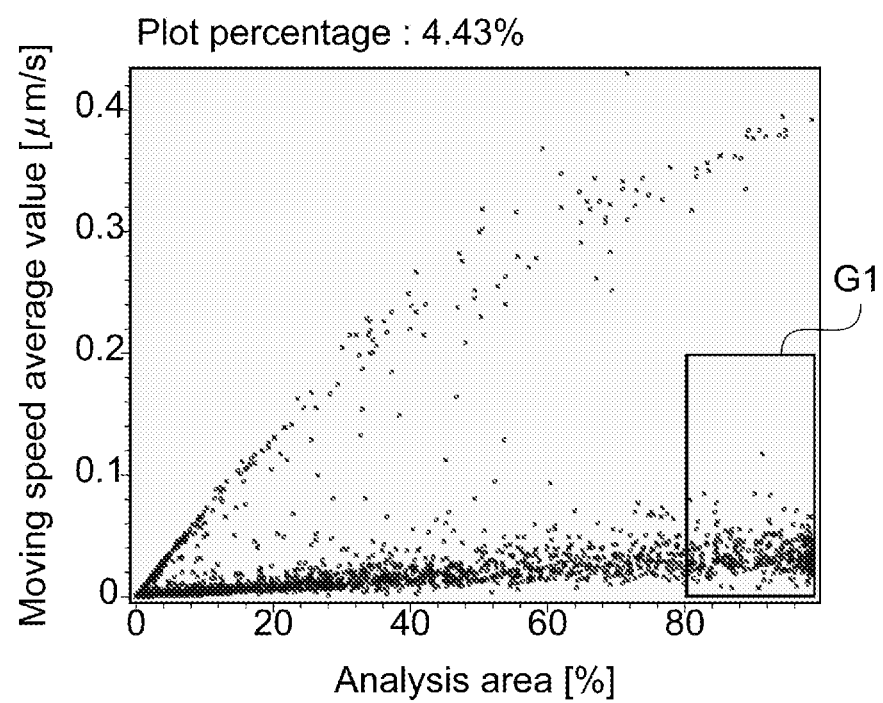
FIG. 20 A plot diagram according to an embodiment of the present technology.
Figure 21:
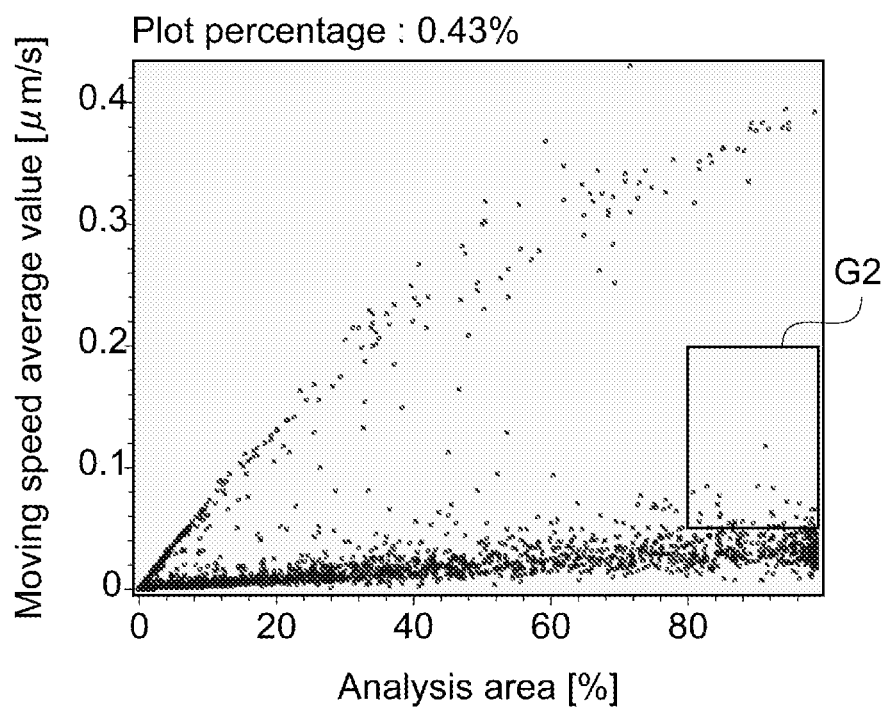
FIG. 21 A plot diagram according to an embodiment of the present technology.

FIG. 19 is a moving image of lung cancer cells (H1975 cell). The whole moving image shown in FIG. 19 was zoned to set the analysis range, and calculated a variety of feature amounts for each analysis range. FIG. 20 and FIG. 21 are plots with the analysis area as the X axis and with the average value of the moving speed as the Y axis.

Figure 22:
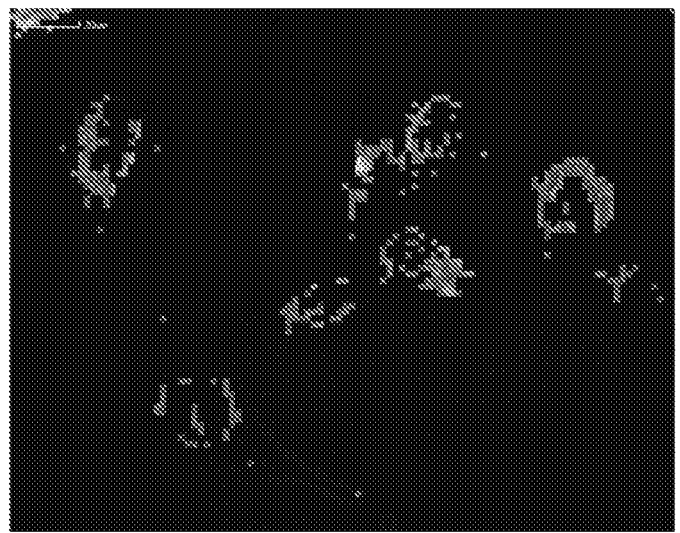
FIG. 22 An analysis image according to an embodiment of the present technology.

As shown in FIG. 20, a range of X axis: 80 to 99%, Y axis: 0 to 0.2 μm/s (G1 in FIG. 20) was gated as the gating range. FIG. 22 shows an analysis image generated by masking the analysis range other than the analysis range corresponding to the gated plot (included in gating range G1).

Figure 23:
FIG. 23 An analysis image according to an embodiment of the present technology.

As shown in FIG. 21, a range of X axis: 80 to 99%, Y axis: 0.05 to 0.2 μm/s (G2 in FIG. 21) was gated as the gating range. FIG. 23 shows the analysis image generated by masking the analysis range other than the analysis range corresponding to the gated plot (included in gating range G2).

Figure 24:
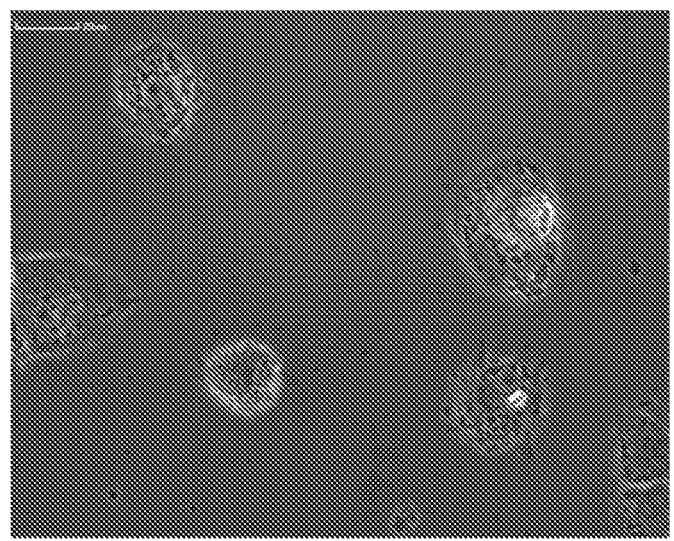
FIG. 24 A moving image according to an embodiment of the present technology.
Figure 25:
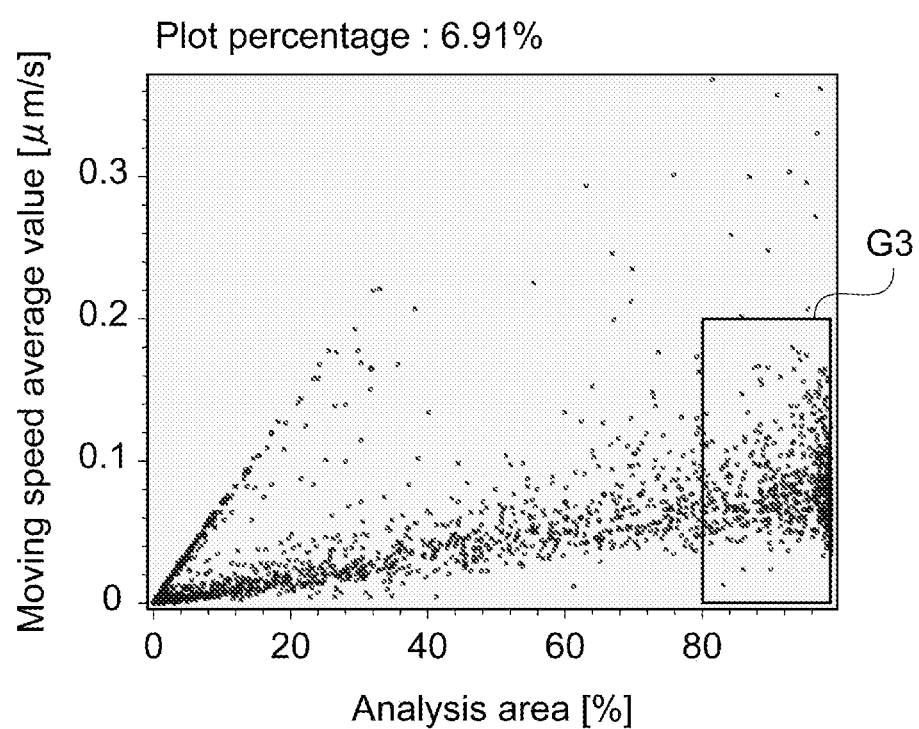
FIG. 25 A plot diagram according to an embodiment of the present technology.
Figure 26:
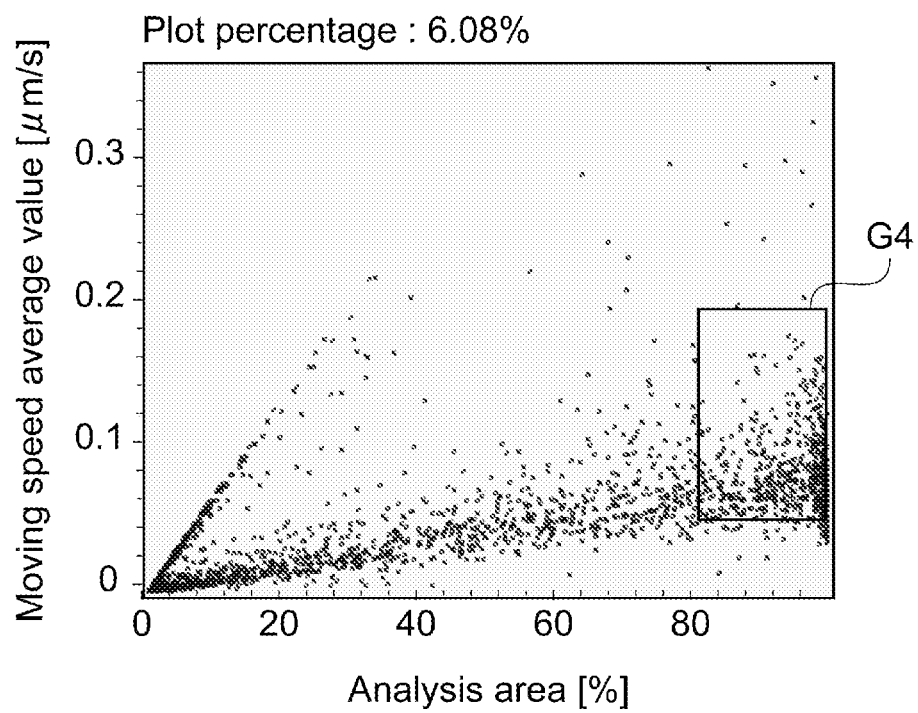
FIG. 26 A plot diagram according to an embodiment of the present technology.

FIG. 24 is a moving image of other of lung cancer cells (H358 cell). The whole moving image shown in FIG. 19 was zoned to set the analysis range, and calculated a variety of feature amounts for each analysis range. FIG. 25 and FIG. 26 are plots with the analysis area as the X axis and with the average value of the moving speed as the Y axis.

Figure 27:
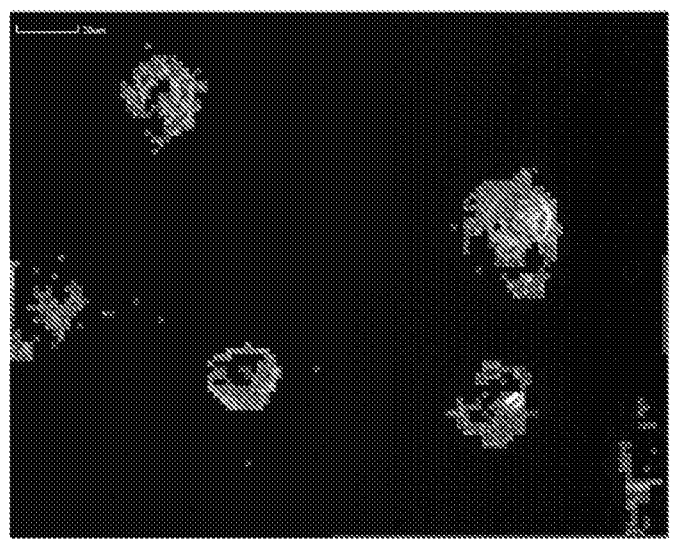
FIG. 27 An analysis image according to an embodiment of the present technology.

As shown in FIG. 25, a range of X axis: 80 to 99%, Y axis: 0 to 0.2 μm/s (G3 in FIG. 25) was gated as the gating range. FIG. 27 shows an analysis image generated by masking the analysis range other than the analysis range corresponding to the gated plot (included in gating range).

Figure 28:
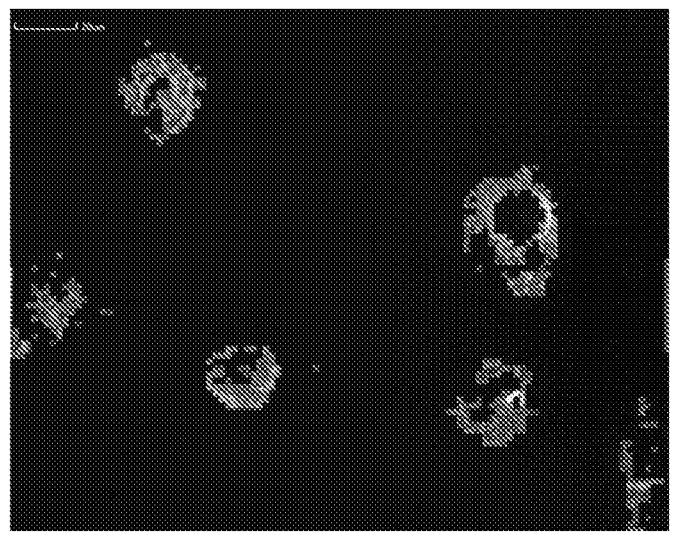
FIG. 28 An analysis image according to an embodiment of the present technology.

As shown in FIG. 26, a range of X axis: 80 to 99%, Y axis: 0.05 to 0.2 μm/s (G4 in FIG. 26) was gated as the gating range. FIG. 28 shows the analysis image generated by masking the analysis range other than the analysis range corresponding to the gated plot.

When FIG. 22 is compared with FIG. 23, the gated (not masked) areas are greatly different. In contrast, when FIG.

27 is compared with FIG. 28, a difference between the gated areas is small. It is therefore shown that the movement of the lung cancer cells shown in FIG. 19 is at low speed, and the movement of the lung cancer cells shown in FIG. 24 is at high speed.

Also, using the information processing apparatus as described in the embodiments, an effect of a gap junction inhibitor (glycyrrhizinate) on cardiac muscle cells was evaluated.

An moving image provided by capturing cultured cardiac muscle cells (hereinafter, moving image M 1), a moving image provided by capturing cultured cardiac muscle cells to which a low concentration of glycyrrhetinic acid is administered (hereinafter, moving image M 2), and a moving image provided by capturing cultured cardiac muscle cells to which a high concentration of glycyrrhetinic acid is administered (hereinafter, moving image M 3) are analyzed.

Figure 29:
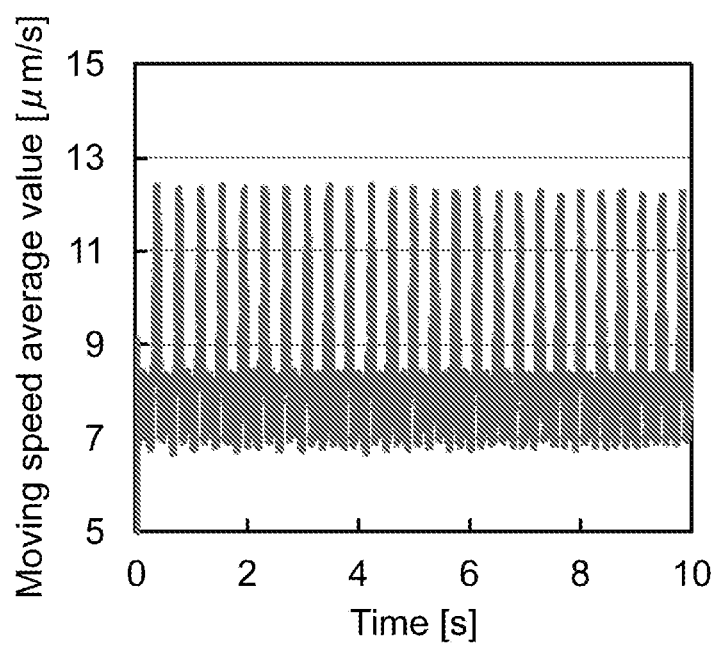
FIG. 29 A graph showing a time change of a feature amount according to an embodiment of the present technology.
Figure 30:
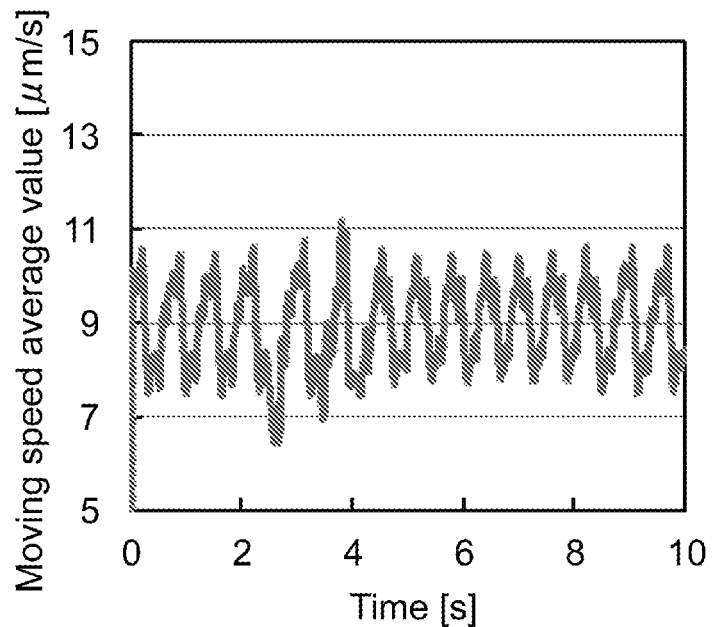
FIG. 30 A graph showing a time change of a feature amount according to an embodiment of the present technology.
Figure 31:
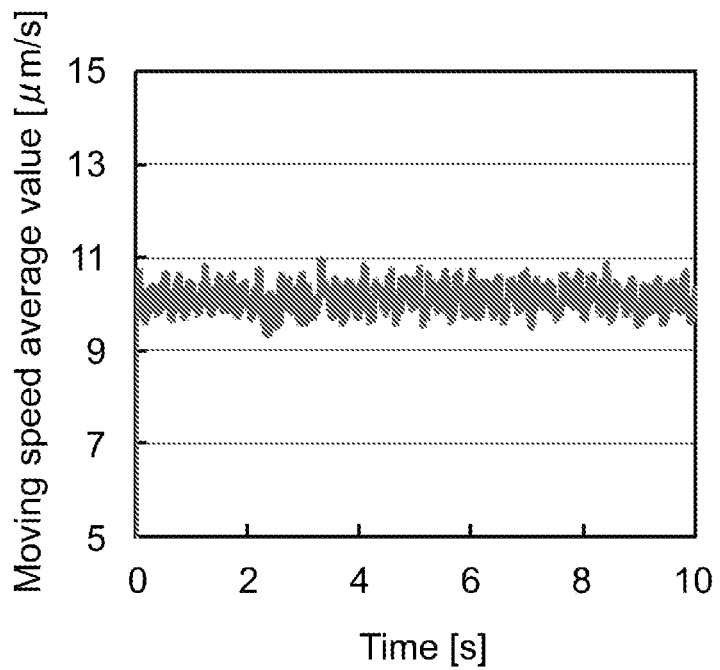
FIG. 31 A graph showing a time change of a feature amount according to an embodiment of the present technology.

For each moving image, the whole moving image is zoned to set the analysis range, and the feature amount for each analysis range is calculated. FIG. 29 shows a time change of the moving speed for a specific analysis range in the moving image M1. FIG. 30 shows a time change of the moving speed for a specific analysis range in the moving image M2. FIG. 31 shows a time change of the moving speed for a specific analysis range in the moving image M3.

Figure 32:
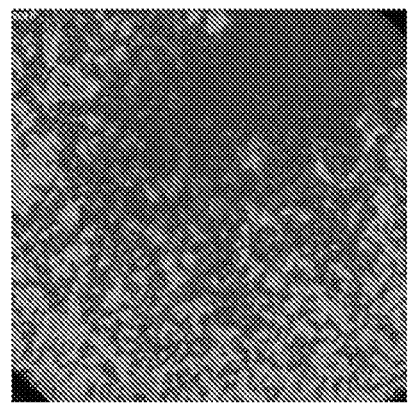
FIG. 32 An image visualizing a feature amount according to an embodiment of the present technology.
Figure 33:
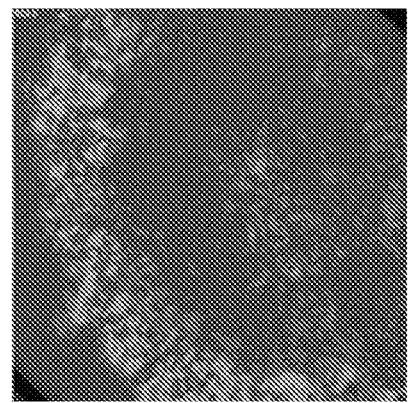
FIG. 33 An image visualizing a feature amount according to an embodiment of the present technology.
Figure 34:
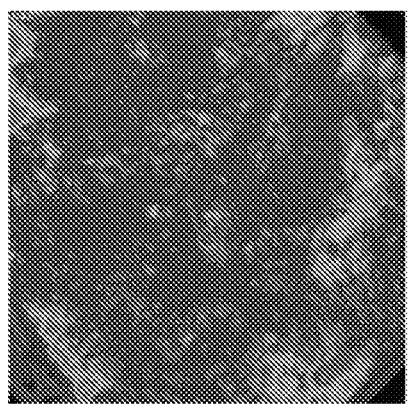
FIG. 34 An image visualizing a feature amount according to an embodiment of the present technology.

FIG. 32 is an image generated by adding shading to an average value of the moving speed per analysis range of the moving image M1. FIG. 33 is an image generated by adding shading to an average value of the moving speed per analysis range of the moving image M2. FIG. 34 an image generated by adding shading to an average value of the moving speed per analysis range of the moving image M3.

As shown in FIG. 33, in the cardiac muscle cells to which a low concentration of glycyrrhetinic acid is administered, a propagation delay is generated. As shown in FIG. 34, in the cardiac muscle cells to which a high concentration of glycyrrhetinic acid is administered, partial desynchronization is generated.

Figure 35:
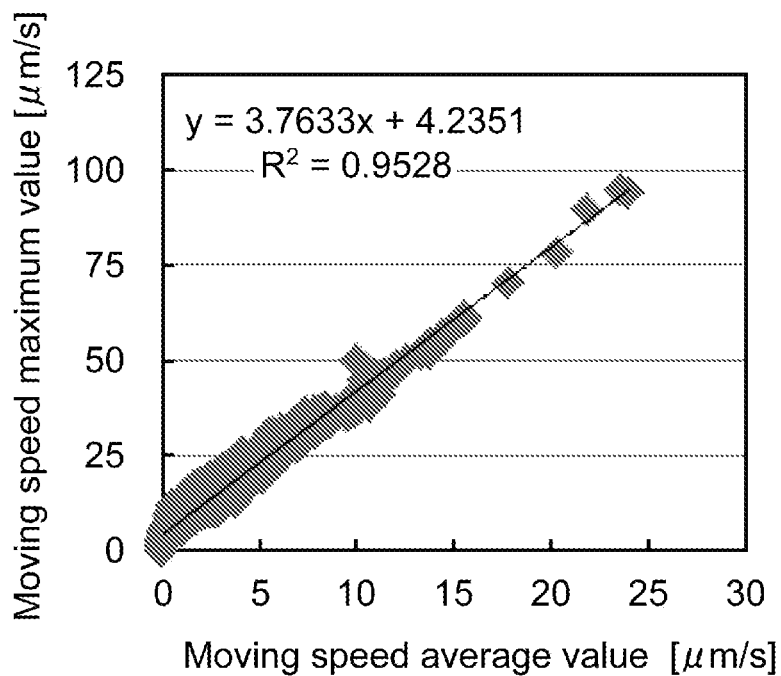
FIG. 35 A plot diagram according to an embodiment of the present technology.
Figure 36:
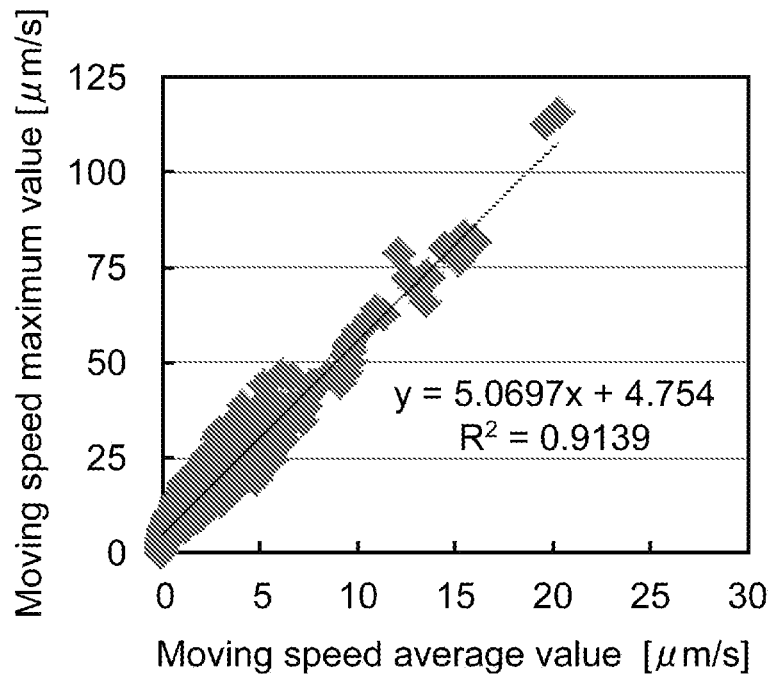
FIG. 36 A plot diagram according to an embodiment of the present technology.
Figure 37:
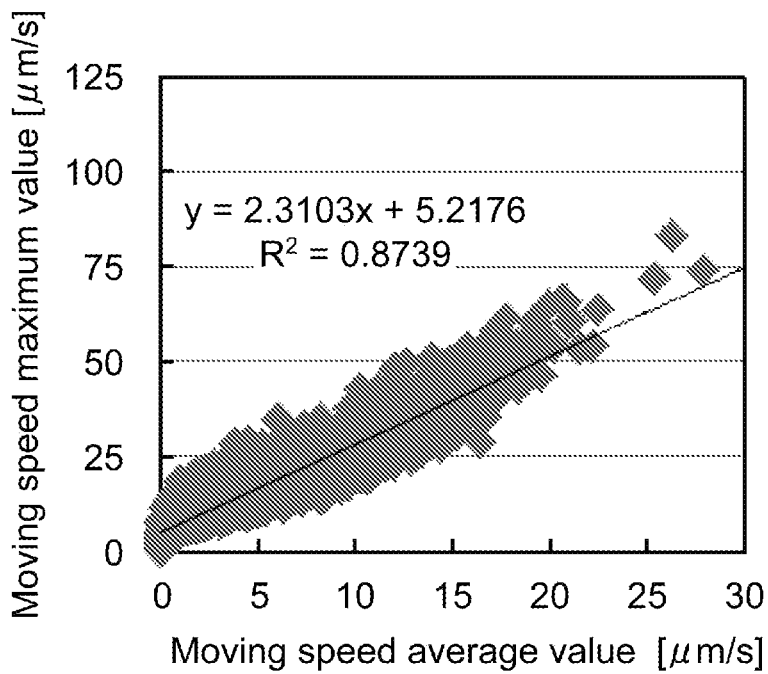
FIG. 37 A plot diagram according to an embodiment of the present technology.

The average value of the moving speed is plotted on the X axis, and the maximum value of the moving speed is plotted on the Y axis. FIG. 35 is a plot diagram generated from the moving image M1. FIG. 36 is a plot diagram generated from the moving image M2. FIG. 37 is a plot diagram generated from the moving image M3.

When FIG. 36 is compared with FIG. 35, it shows that, by administrating the cardiac muscle cells to a low concentration of glycyrrhetinic acid, a pulsation speed (the maximum value of the moving speed) is increased, and a pulsation number (the average value of the moving speed) is decreased. Furthermore, it shows that a deviation of the pulsation number is increased (a correlation between the average value and the maximum value of the moving speed is decreased).

When FIG. 37 is compared with FIG. 35, it shows that, by administrating the cardiac muscle cells to a high concentration of glycyrrhetinic acid, a pulsation speed (the maximum value of the moving speed) is decreased, and a pulsation number (the average value of the moving speed) is increased. Furthermore, it shows that a deviation of the pulsation number is increased (a correlation between the average value and the maximum value of the moving speed is decreased).

Figure 38:
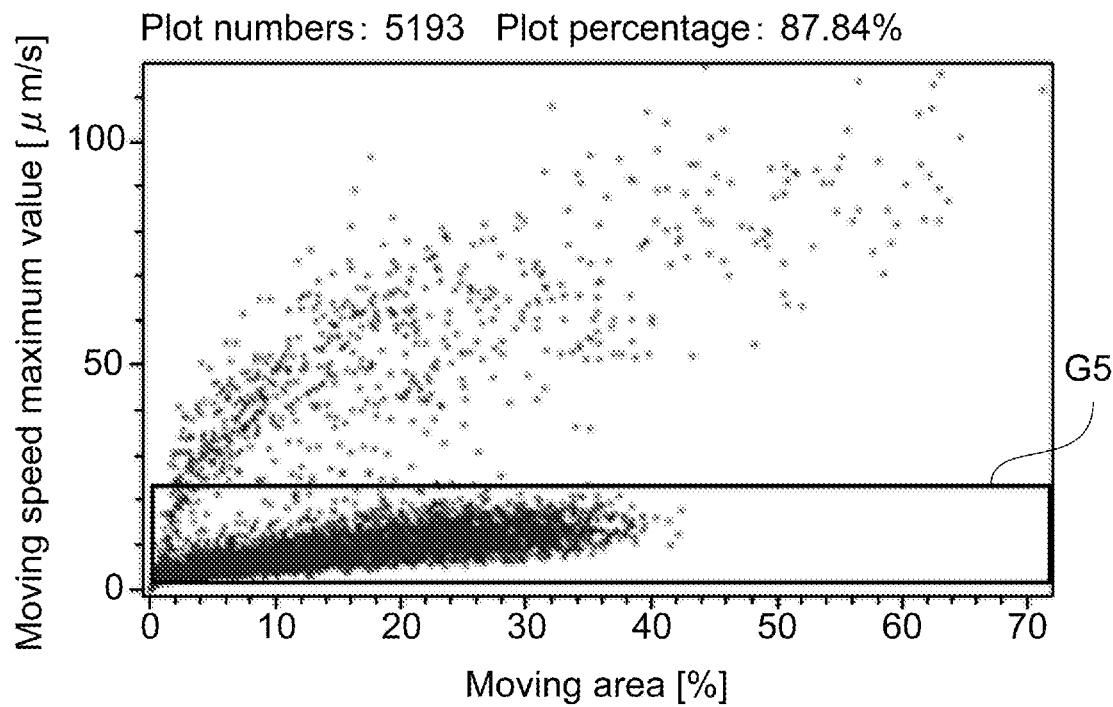
FIG. 38 A plot diagram according to an embodiment of the present technology.
Figure 39:
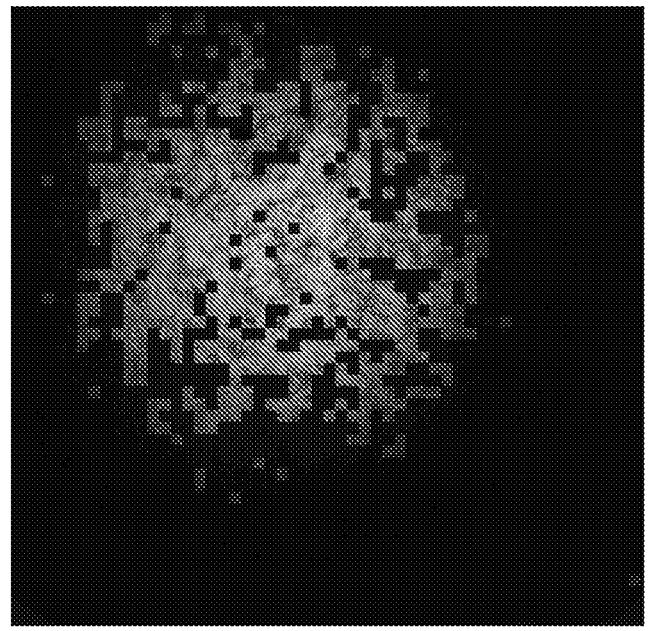
FIG. 39 An analysis image according to an embodiment of the present technology.

The whole moving image was zoned to set the analysis range, and a variety of characteristic amounts were calculated for each analysis range. FIG. 38 is a plot with the moving area as the X axis, and with the maximum value of the moving speed as the Y axis. As shown in FIG. 38, a range of X axis: 0 to 72%, Y axis: 1 to 23 µm/s (G5 in FIG. 38) was gated as the gating range. FIG. 39 shows an example of an analysis image generated by masking the analysis range other than the analysis range corresponding to the gated plot.

By plotting the moving area in the X axis, and the maximum value or the average value of the moving speed in the Y axis and selecting the area having the maximum value or the average value exceeding the predetermined value, a surface area of the moving area can be calculated. The calculation of the surface area of the moving area allows evaluation of a state of the cells upon a medical assay and evaluation of muscle cells upon differentiation.

Figure 40:
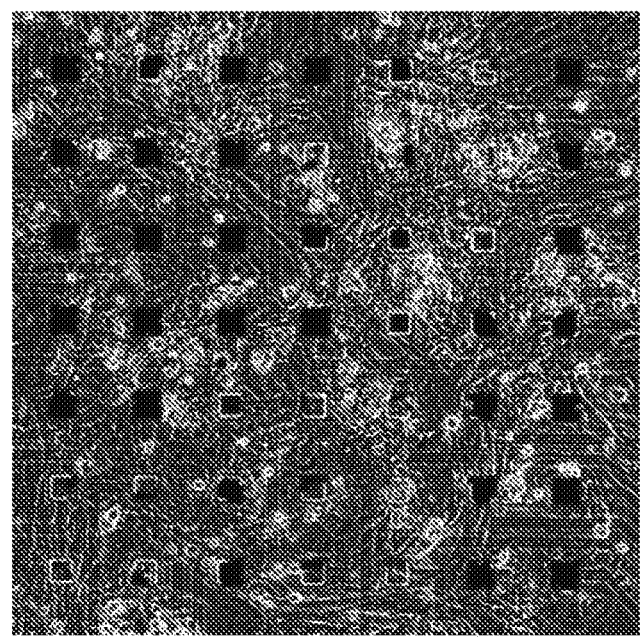
FIG. 40 A moving image according to an embodiment of the present technology.
Figure 41:
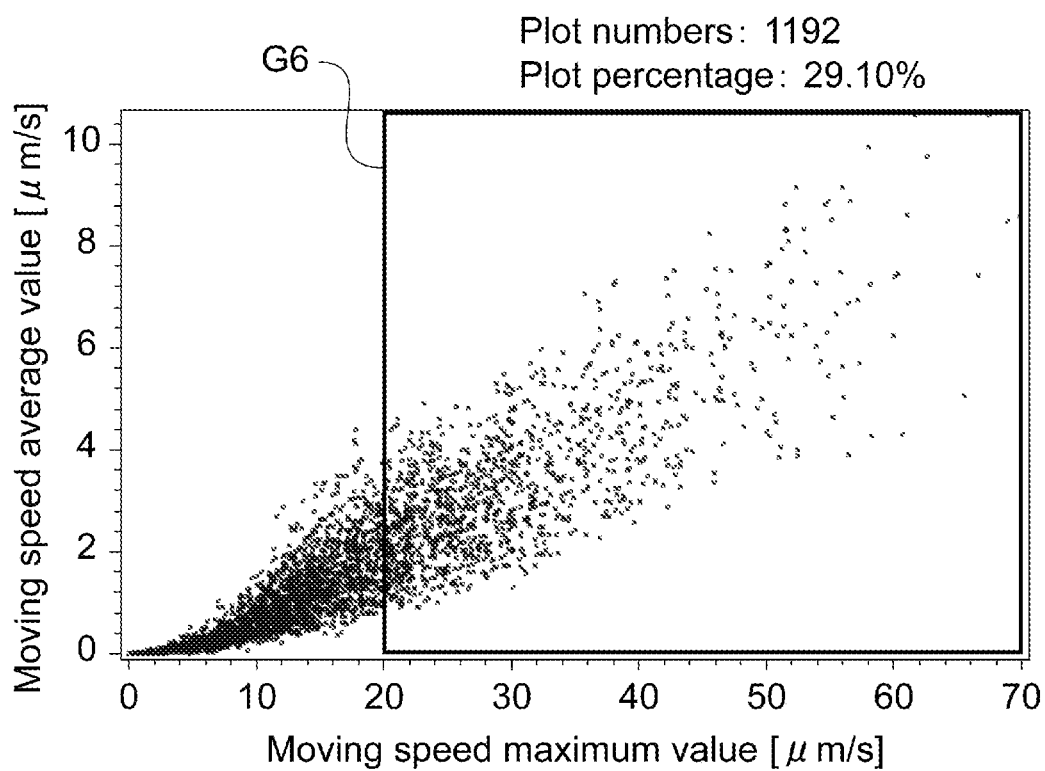
FIG. 41 A plot diagram according to an embodiment of the present technology.
Figure 42:
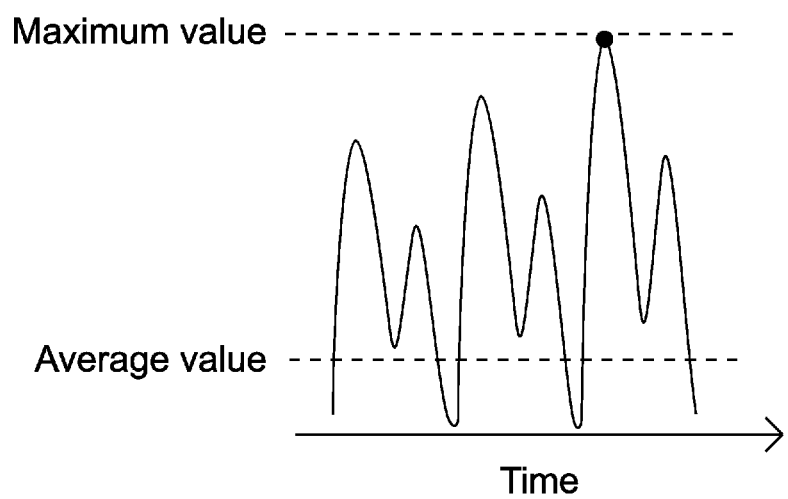
FIG. 42 A schematic diagram showing a waveform pattern of the movement according to an embodiment of the present technology.

FIG. 40 is an moving image provided by capturing an electrode and cardiac muscle cells. The whole moving image was zoned to set the analysis range, and a variety of characteristic amounts were calculated for each analysis range. FIG. 41 is a plot with the maximum value of the moving speed as the X axis and the average value of the moving speed as the Y axis extracted from the moving image. FIG. 42 is a schematic diagram showing a waveform pattern of the movement.

As shown in FIG. 41, a range of X axis: 20 to 70% (G6 in FIG. 41) was gated as the gating range. As shown in FIG. 42, the maximum values of the moving speed each having a certain height were taken out. A plot of the maximum values of the moving speed exceeding 20% was 29.1%. It concludes that the parts functioning as the cardiac muscle occupy 30%.

Figure 43:
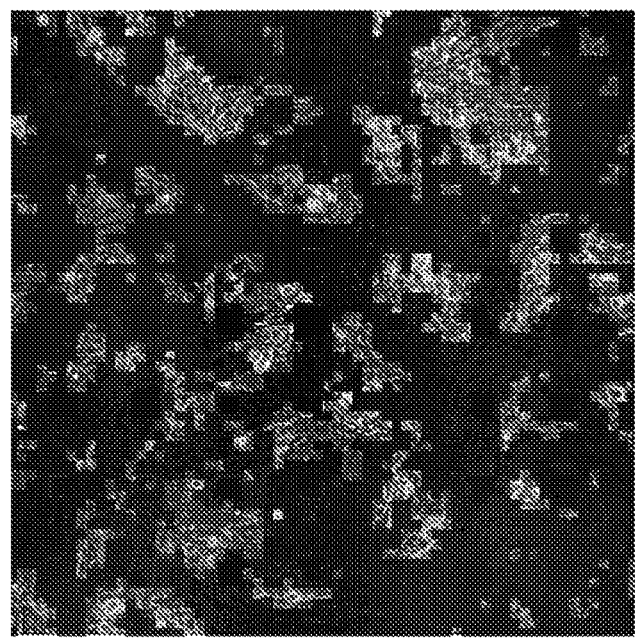
FIG. 43 A moving image according to an embodiment of the present technology.

FIG. 43 is an analysis image for visualizing a result of the gating, and shows the analysis image generated by masking the analysis range other than the analysis range corresponding to the gated plot.

In this manner, by calculating and plotting a similarity degree to a specific waveform pattern for each analysis range, it is possible to specify the area other than a noise occurrence area or to specify normal cells or abnormal cells.

The noise occurrence area often has a waveform pattern different from normal. Therefore, by specifying the areas having the predetermined value or more of the similarity degree to the specific waveform pattern, it is possible to specify the area other than the noise occurrence area.

If the waveform patterns are different in the normal cells and the abnormal cells, it is possible to classify by calculating the similarity degree between the waveform patterns of the normal cells and the abnormal cells. This also applies to the characteristic amount such as the number of occurrences of the specific waveform pattern for each analysis range.

Figure 44:
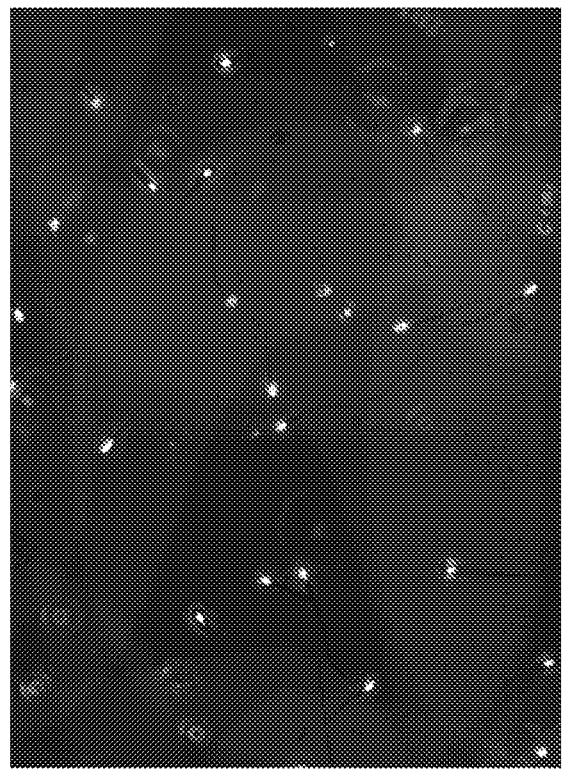
FIG. 44 A moving image according to an embodiment of the present technology.
Figure 45:
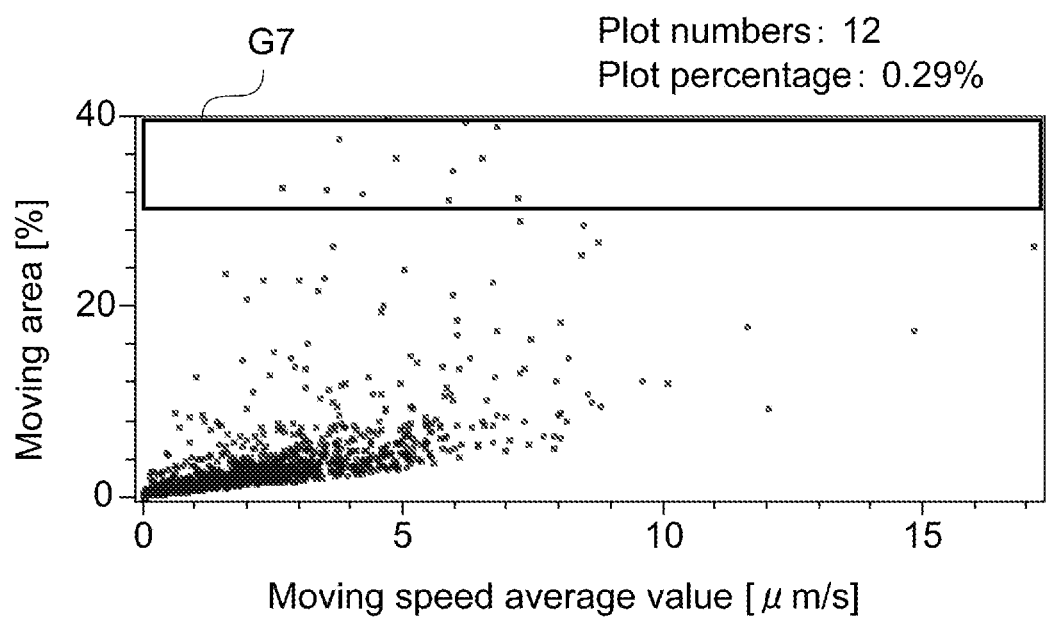
FIG. 45 A plot diagram according to an embodiment of the present technology.

FIG. 44 is a moving image of sperms captured. The whole moving image was zoned to set the analysis range, and a variety of characteristic amounts were calculated for each analysis range. FIG. 45 is a plot with the average value of the moving speed as the X axis and the moving area as the Y axis extracted from the moving image.

Figure 46:
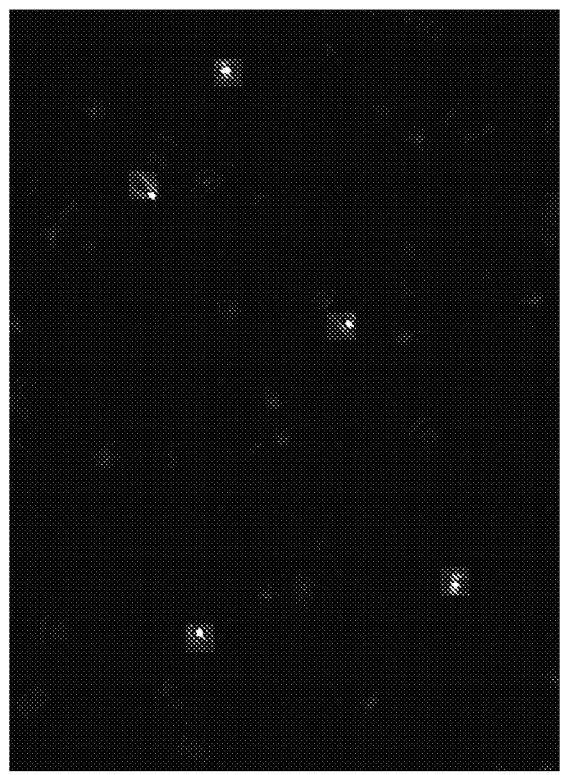
FIG. 46 An analysis image according to an embodiment of the present technology.

As shown in FIG. 45, a range of Y axis: 30 to 40% (G7 in FIG. 45) was gated as the gating range. FIG. 46 is an analysis image for visualizing a result of the gating, and shows the analysis image generated by masking the analysis range other than the analysis range corresponding to the gated plot.

In this manner, by plotting the object to be observed such as sperms that move vigorously and specifying the moving area that is continuously large, it is possible to specify the area of the object to be observed that moves slow or is abnormal. By dividing the surface area of the area by the area of one object to be observed, the number may be counted. In the case of sperms, a sperm mobility can be determined by calculating the number of the sperms that do not move in the object to be observed.

The present technology may have the following configurations.

(1) An image processing apparatus including:
circuitry configured to:
receive at least two images of a biological sample;
determine motion information for a plurality of regions of the at least two images, wherein the motion information corresponds to motion of the biological sample; and
generate a graphical representation of at least two characteristic amounts, wherein the at least two characteristic amounts correspond to a region of the plurality of regions and one characteristic amount of the at least two characteristic amounts is indicative of the motion information.

(2) The image processing apparatus of claim (1), wherein the graphical representation has a first axis corresponding to a first characteristic of the motion information and a second axis corresponding to a second characteristic.

(3) The image processing apparatus of claim (2), wherein the graphical representation is a two-dimensional plot diagram of the at least two characteristic amounts on the first axis and the second axis.

(4) The image processing apparatus of claim (2), wherein the first characteristic is an average value, a maximum value, a standard deviation, a rate of acceleration, a frequency value, an integrated value, a percentage of area having movement above a predetermined threshold, a level of similarity with a waveform pattern, or a number of times when a level of similarity with a waveform pattern is above a predetermined threshold.

(5) The image processing apparatus of claim (4), wherein the second characteristic is an average value, a maximum value, a standard deviation, a rate of acceleration, a frequency value, an integrated value, a motion area, a level of similarity with a waveform, or a number of times when showing specific waveform.

(6) The image processing apparatus of claim (4), wherein the second characteristic is an average value, a maximum value, a minimum value, a standard deviation, or an area percentage occupied by the biological sample.

(7) The image processing apparatus of claim (2), wherein the method further includes determining the at least two characteristic amounts by determining the first characteristic and the second characteristic for each region of the plurality of regions.

(8) The image processing apparatus of claim (1), wherein the biological sample includes at least a portion of a cell, at least a portion of a tissue, or at least a portion of an animal.

(9) The image processing apparatus of claim (1), wherein the method further includes receiving input indicating a portion of the at least two characteristic amounts.

(10) The image processing apparatus of claim (9), wherein the method further includes presenting aggregate information for the portion of the at least two characteristic amounts, wherein the aggregate information indicates an amount of regions corresponding to the portion of the at least two characteristic amounts.

(11) The image processing apparatus of claim (9), wherein the method further includes generating an analysis image by superimposing on an image of the at least two images a mask at positions in the image excluded by regions corresponding to the portion of the at least two characteristic amounts.

(12) The image processing apparatus of claim (11), wherein the analysis image includes a number of regions equal to a number of data points in the graphical representation.

(13) The image processing apparatus of claim (11), wherein the analysis image provides an indication of an area of the biological sample that is moving over a time duration corresponding to the at least two images.

(14) The image processing apparatus of claim (11), wherein the analysis image provides an indication of an area of the biological sample that is inactive over a time duration corresponding to the at least two images.

(15) The image processing apparatus of claim (1), wherein the graphical representation includes a second set of at least two characteristic amounts corresponding to a second set of images and the culture environment of the biological sample is different between the at least two images and the second set of images.

(16) The image processing apparatus of claim (15), wherein the at least two images are acquired before the addition of a medical agent to the biological sample and the second set of images are acquired after the addition of the medical agent to the biological sample.

(17) The image processing apparatus of claim (1), wherein the at least two images are acquired over a time duration, and the method further includes determining the motion information for the time duration by analyzing the at least two images.

(18) The image processing apparatus of claim (17), wherein analyzing the at least two images includes determining a feature of the biological sample and determining regions of the plurality of regions that include the feature.

(19) The image processing apparatus of claim (17), wherein analyzing the at least two images includes determining a motion vector corresponding to movement of a group of pixels between a first image of the at least two images and a second image of the at least two images.

(20) An imaging processing method including:
receiving at least two images of a biological sample;
determining motion information for a plurality of regions of the at least two images, wherein the motion information corresponds to motion of the biological sample; and
generating a graphical representation of at least two characteristic amounts, wherein the at least two characteristic amounts correspond to a region of the plurality of regions and one characteristic amount of the at least two characteristic amounts is indicative of the motion information.

(21) The imaging processing method of claim (20), wherein the method further includes presenting the graphical representation on a display.

(22) The image processing apparatus of claim (21), wherein the method further includes receiving, from the display, input indicating a selected portion of data values in the graphical representation and presenting an analysis image on the display, wherein the analysis image indicates regions of an image of the at least two images corresponding to the selected portion of data values.

(23) An imaging processing system including:
at least one image sensor configured to acquire at least two images of a biological sample; and
circuitry configured to:
receive the at least two images from the at least one image sensor;

determine motion information for a plurality of regions of the at least two images, wherein the motion information corresponds to motion of the biological sample; and generate a graphical representation of at least two characteristic amounts, wherein the at least two characteristic amounts correspond to a region of the plurality of regions and one characteristic amount of the at least two characteristic amounts is indicative of the motion information.

(24) The imaging processing system of claim (23), the imaging processing system further including a microscope optical system, wherein the at least one image sensor is configured to detect light from the microscope optical system.

(25) The imaging processing system of claim (23), the imaging processing system further including a display configured to present the graphical representation.

(26) The imaging processing system of claim (25), wherein the display is further configured to receive user input indicating a selection of an area of the graphical representation, wherein the area includes a plurality of data values of the graphical representation.

(27) The imaging processing system of claim (26), wherein the display is further configured to display an analysis image based on the selected area in response to receiving the user input.

(28) An information processing apparatus, including:
a characteristic amount extracting unit for extracting a first characteristic amount from at least two images captured at different times included in a moving image where an object to be observed is captured over time, and extracting a second characteristic amount from at least one image included in the moving image; and
a plot generating unit for generating a plot diagram by plotting the first characteristic amount and the second characteristic amount.

(29) The characteristic amount extracting unit according to (28) above, in which the characteristic amount extracting unit extracts the second characteristic amount from at least two images captured at different times included in the moving image.

(30) The information processing apparatus according to (28) or (29) above, further including:
a range setting unit for setting an analysis range in the moving image, in which
the characteristic amount extracting unit extracts the first characteristic amount and the second characteristic amount per analysis range, and
the plot generating unit generates a plot diagram by plotting the first characteristic amount and the second characteristic amount per analysis range.

(31) The information processing apparatus according to any one of (28) to (30) above, further including:
a gating unit for gating the plot.

(32) The information processing apparatus according to any one of (28) to (31) above, further including:
an analysis image generating unit for visualizing a result of the gating by the gating unit, and for generating an analysis image.

(33) The information processing apparatus according to any one of (32) to (33) above, in which
the range setting unit performs image processing on the moving image, and sets the analysis range based on a result of the image processing.

(34) The information processing apparatus according to any one of (28) to (33) above, in which
the moving image includes the first moving image and the second moving image where the object to be observed is captured under different conditions, and
the plot generating unit generates a plot diagram by plotting a first characteristic amount and a second characteristic amount extracted from the first moving image and the first characteristic amount and the second characteristic amount extracted from the second moving image.

(35) The information processing apparatus according to any one of (28) to (34) above, in which
the characteristic amount extracting unit performs movement analysis processing on the moving image, and extracts the first characteristic amount based on a result of the movement analysis processing.

(36) A program for functioning an information processing apparatus, including:
a characteristic amount extracting unit for extracting a first characteristic amount from at least two images captured at different times included in a moving image where an object to be observed is captured over time, and extracting a second characteristic amount from at least one image included in the moving image; and
a plot generating unit for generating a plot diagram by plotting the first characteristic amount and the second characteristic amount.

(37) An information processing method, including:
extracting a first characteristic amount from at least two images captured at different times included in a moving image where an object to be observed is captured over time;
extracting a second characteristic amount from at least one image included in the moving image by a characteristic amount extracting unit; and
generating a plot diagram by plotting the first characteristic amount and the second characteristic amount by a plot generating unit.

(38) An observation system, including:
an image capturing apparatus for capturing an object to be observed over time, and generating a moving image; and
an information processing apparatus including a characteristic amount extracting unit for extracting a first characteristic amount from at least two images captured at different times included in the moving image where an object to be observed is captured over time, and extracting a second characteristic amount from at least one image included in the moving image, and a plot generating unit for generating a plot diagram by plotting the first characteristic amount and the second characteristic amount.

REFERENCE SIGNS LIST 1 observation system
11 image capturing apparatus
12 information processing apparatus
121 moving image acquiring unit
122 range setting unit
123 feature amount extracting unit
124 plot generating unit
125 gating unit
126 analysis image generating unit
127 image outputting unit
128 analysis image generating unit

The invention claimed is:

1. An image processing apparatus comprising:
circuitry configured to:
receive at least two images of a biological sample, wherein the biological sample includes at least a portion of a cell, at least a portion of a tissue, or at least a portion of an animal;
determine motion information for a plurality of regions of the at least two images, wherein the motion information corresponds to motion of the biological sample; and
generate a graphical representation of at least two characteristic amounts, wherein the at least two characteristic amounts correspond to a region of the plurality of regions and one characteristic amount of the at least two characteristic amounts is indicative of the motion information, wherein:
the graphical representation has a first axis corresponding to a first characteristic of the motion information and a second axis corresponding to a second characteristic,
the first characteristic is an average value, a maximum value, a standard deviation, a rate of acceleration, a frequency value, an integrated value, a percentage of area having movement above a predetermined threshold, a level of similarity with a waveform pattern, or a number of times when a level of similarity with a waveform pattern is above a predetermined threshold, and
the second characteristic is an average value, a maximum value, a minimum value, a standard deviation, a rate of acceleration, a frequency value, an integrated value, a motion area, a level of similarity with a waveform, a number of times when showing specific waveform, or an area percentage occupied by the biological sample.

2. The image processing apparatus of claim 1, wherein the graphical representation is a two-dimensional plot diagram of the at least two characteristic amounts on the first axis and the second axis.

3. The image processing apparatus of claim 1, wherein the circuitry is further configured to determine the at least two characteristic amounts by determining the first characteristic and the second characteristic for each region of the plurality of regions.

4. The image processing apparatus of claim 1, wherein the circuitry is further configured to receive input indicating a portion of the at least two characteristic amounts.

5. The image processing apparatus of claim 4, wherein the circuitry is further configured to present aggregate information for the portion of the at least two characteristic amounts, wherein the aggregate information indicates an amount of regions corresponding to the portion of the at least two characteristic amounts.

6. The image processing apparatus of claim 4, wherein the circuitry is further configured to generate an analysis image by superimposing on an image of the at least two images a mask at positions in the image excluded by regions corresponding to the portion of the at least two characteristic amounts.

7. The image processing apparatus of claim 6, wherein the analysis image includes a number of regions equal to a number of data points in the graphical representation.

8. The image processing apparatus of claim 6, wherein the analysis image provides an indication of an area of the biological sample that is moving over a time duration corresponding to the at least two images.

9. The image processing apparatus of claim 6, wherein the analysis image provides an indication of an area of the biological sample that is inactive over a time duration corresponding to the at least two images.

10. The image processing apparatus of claim 1, wherein the graphical representation includes a second set of at least two characteristic amounts corresponding to a second set of images and the culture environment of the biological sample is different between the at least two images and the second set of images.

11. The image processing apparatus of claim 10, wherein the at least two images are acquired before the addition of a medical agent to the biological sample and the second set of images are acquired after the addition of the medical agent to the biological sample.

12. The image processing apparatus of claim 1, wherein the at least two images are acquired over a time duration, and the circuitry is further configured to determine the motion information for the time duration by analyzing the at least two images.

13. The image processing apparatus of claim 12, wherein analyzing the at least two images comprises determining a feature of the biological sample and determining regions of the plurality of regions that include the feature.

14. The image processing apparatus of claim 12, wherein analyzing the at least two images comprises determining a motion vector corresponding to movement of a group of pixels between a first image of the at least two images and a second image of the at least two images.

15. An imaging processing method comprising:
receiving at least two images of a biological sample, wherein the biological sample includes at least a portion of a cell, at least a portion of a tissue, or at least a portion of an animal;
determining motion information for a plurality of regions of the at least two images, wherein the motion information corresponds to motion of the biological sample; and
generating a graphical representation of at least two characteristic amounts, wherein the at least two characteristic amounts corresponds to a region of the plurality of regions and one of the at least two characteristic amounts is indicative of the motion information, wherein:
the graphical representation has a first axis corresponding to a first characteristic of the motion information and a second axis corresponding to a second characteristic,
the first characteristic is an average value, a maximum value, a standard deviation, a rate of acceleration, a frequency value, an integrated value, a percentage of area having movement above a predetermined threshold, a level of similarity with a waveform pattern, or a number of times when a level of similarity with a waveform pattern is above a predetermined threshold, and
the second characteristic is an average value, a maximum value, a minimum value, a standard deviation, a rate of acceleration, a frequency value, an integrated value, a motion area, a level of similarity with a waveform, a number of times when showing specific waveform, or an area percentage occupied by the biological sample.

16. The imaging processing method of claim 15, wherein the method further comprises presenting the graphical representation on a display.

17. The imaging processing method of claim 16, wherein the method further comprises receiving, from the display, input indicating a selected portion of data values in the graphical representation and presenting an analysis image on the display, wherein the analysis image indicates regions of an image of the at least two images corresponding to the selected portion of data values.

18. An imaging processing system comprising:
at least one image sensor configured to acquire at least two images of a biological sample, wherein the biological sample includes at least a portion of a cell, at least a portion of a tissue, or at least a portion of an animal; and
circuitry configured to:
receive the at least two images from the at least one image sensor;
determine motion information for a plurality of regions of the at least two images, wherein the motion information corresponds to motion of the biological sample; and
generate a graphical representation of at least two characteristic amounts, wherein the at least two characteristic amounts correspond to a region of the plurality of regions and one characteristic amount of the at least two characteristic amounts is indicative of the motion information, wherein:
the graphical representation has a first axis corresponding to a first characteristic of the motion information and a second axis corresponding to a second characteristic,
the first characteristic is an average value, a maximum value, a standard deviation, a rate of acceleration, a frequency value, an integrated value, a percentage of area having movement above a predetermined threshold, a level of similarity with a waveform pattern, or a number of times when a level of similarity with a waveform pattern is above a predetermined threshold, and
the second characteristic is an average value, a maximum value, a minimum value, a standard deviation, a rate of acceleration, a frequency value, an integrated value, a motion area, a level of similarity with a waveform, a number of times when showing specific waveform, or an area percentage occupied by the biological sample.

19. The imaging processing system of claim 18, the imaging processing system further comprising a microscope optical system, wherein the at least one image sensor is configured to detect light from the microscope optical system.

20. The imaging processing system of claim 18, the imaging processing system further comprising a display configured to present the graphical representation.

21. The imaging processing system of claim 20, wherein the display is further configured to receive user input indicating a selection of an area of the graphical representation, wherein the area includes a plurality of data values of the graphical representation.

22. The imaging processing system of claim 21, wherein the display is further configured to display an analysis image based on the selected area in response to receiving the user input.

23. The image processing apparatus of claim 1, wherein the circuitry is further configured to set, based on user input, a size for the plurality of regions, and determining the motion information further comprises determining portions of the at least two images having the size as the plurality of regions.

* * * * *